(12) United States Patent
Schultz et al.

(10) Patent No.: US 7,429,729 B2
(45) Date of Patent: Sep. 30, 2008

(54) MULTI-BEAM ION MOBILITY TIME-OF-FLIGHT MASS SPECTROMETER WITH BIPOLAR ION EXTRACTION AND ZWITTERION DETECTION

(75) Inventors: J. Albert Schultz, Houston, TX (US); Valeri V. Raznikov, Moscow (RU); Thomas F. Egan, Houston, TX (US); Michael V. Ugarov, Houston, TX (US); Agnès Tempez, Houston, TX (US); Marina O. Raznikova, Moscow (RU); Valentin A. Tarasenko, Chernoglovka (RU)

(73) Assignee: Ionwerks, Inc., Houston, TX (US)

( * ) Notice: Subject to any disclaimer, the term of this patent is extended or adjusted under 35 U.S.C. 154(b) by 295 days.

(21) Appl. No.: 11/441,768

(22) Filed: May 26, 2006

(65) Prior Publication Data

US 2006/0289747 A1 Dec. 28, 2006

Related U.S. Application Data

(60) Provisional application No. 60/685,240, filed on May 27, 2005.

(51) Int. Cl.
*H01J 49/00* (2006.01)
(52) U.S. Cl. ........................ 250/287; 250/286
(58) Field of Classification Search ................ 250/287, 250/286
See application file for complete search history.

(56) References Cited

U.S. PATENT DOCUMENTS

| | | | |
|---|---|---|---|
| 6,559,441 B2 | 5/2003 | Clemmer | |
| 6,642,059 B2 | 11/2003 | Chait et al. | |
| 6,690,004 B2 | 2/2004 | Miller et al. | |
| 6,781,122 B2 | 8/2004 | Colburn et al. | |
| 6,815,671 B2 * | 11/2004 | Johnston et al. | 250/287 |
| 7,170,052 B2 * | 1/2007 | Furutani et al. | 250/287 |
| 7,223,969 B2 * | 5/2007 | Schultz et al. | 250/290 |
| 2001/0032929 A1 | 10/2001 | Fuhrer et al. | |
| 2005/0035284 A1 | 2/2005 | Schultz et al. | |
| 2006/0289746 A1 * | 12/2006 | Raznikov et al. | 250/294 |

FOREIGN PATENT DOCUMENTS

| | | |
|---|---|---|
| GB | 2389704 | 12/2003 |
| GB | 2390935 | 1/2004 |
| WO | WO-03091721 | 11/2003 |

* cited by examiner

*Primary Examiner*—Kiet T Nguyen
(74) *Attorney, Agent, or Firm*—Fulbright & Jaworski, LLP

(57) ABSTRACT

The present invention relates generally to instrumentation and methodology for the characterization of chemical samples in solutions or on a surface which is based on modified ionization methods with or without adjustable pH and controllable H-D exchange in solution, in improved ion mobility spectrometer (IMS), a multi-beam ion per-selection of the initial flow, and coordinated mobility and mass ion separation and detection using a single or several independent time-of-flight mass spectrometers for different beams with methods for fragmenting ion mobility-separated ions and multi-channel data recording.

85 Claims, 14 Drawing Sheets

FIG. 11

MULTI-BEAM ION MOBILITY TIME-OF-FLIGHT MASS SPECTROMETER WITH BIPOLAR ION EXTRACTION AND ZWITTERION DETECTION

RELATED APPLICATIONS

This application claims priority to U.S. provisional application Ser. No. 60/685,240, filed on May 27, 2005.

TECHNICAL FIELD

The present invention relates generally to instrumentation and methodology for the characterization of chemical samples in solutions or on a surface and is based on modified ionization methods with or without adjustable pH and controllable hydrogen-deuterium (H-D) exchange in solution, an improved ion mobility spectrometer (IMS), a multi-beam ion pre-selection of the initial flow, and coordinated mobility and mass ion separation and detection using a single or several independent time-of-flight mass spectrometers (TOFMS) for different beams with methods for fragmenting ion mobility (IM) separated ions and multi-channel data recording.

BACKGROUND OF THE INVENTION

Among a variety of ionization techniques applied to mass spectrometry, electrospray ionization (ESI) has evolved into a powerful and widely practiced tool for the analysis of high molecular weight biological molecules. The success of ESI in the analysis of biomolecules lies in the method's ability to extract fragile chemical species intact from solution in an ionized form, and transfer them to the gas phase for mass analysis. A unique characteristic of the electrospray (ES) ion source is the ability to form multiply-charged ions, which facilitates the analysis of extremely high molecular weight molecules with mass analyzers having relatively low nominal upper mass limits. Electrospray ionization methods have been extensively reviewed. See, for example, reviews by Banks, Jr. and Whitehouse in Methods in Enzymology, Vol. 270, 1996, pp. 486-519; and Smith, R. D., et al., *Analytical Chemistry*, Vol. 62, 1990, pp. 882-899. In an ES ion source, a liquid sample is introduced through a small bore tube that is maintained at several kilovolts at or near atmospheric pressure into a chamber containing a bath gas. A strong electrostatic field at the tip of the tube charges the surface of the emerging liquid generating Coulomb forces sufficient to overcome the liquid's surface tension and to disperse the liquid into a fine spray of charged droplets. After passing through the atmospheric-low pressure interface and desolvation region, ions are injected into a mass spectrometer. For analysis of complex samples, the multicharged ion formation characteristics of Electrospray Ionization Mass Spectrometry (ESI-MS) complicate mass spectral analysis, particularly for high mass biomolecules. Under the current understanding in the art, it is unclear why multicharged ion distributions observed in electrospray mass spectra are so different from the charge distributions of the corresponding ions in solution. For example, ESI mass spectra of positive ionized peptides or proteins are usually collected under pH conditions such that all or nearly all basic amino acid residues inside this peptide are be protonated with a probability extremely close to 1. Essentially, only ions with maximal possible charge are expected to exist in solution but ESI mass spectrum exhibits a wide distribution of multicharged ions. Since charge distributions of ions in solution are well established and since these distributions can be controlled by changes of the solution pH (properly controlling other experimental conditions), it would be highly valuable analytically to develop methods of extracting ions from solution while conserving their equilibrium solution charge distribution. The important property of biomolecules in solution is the isoelectric point, which is determined by the solution pH when the total charge of the biomolecule is zero. Using so called isoelectric focusing, it is possible to achieve good separations of biomolecules in gel electrophoresis techniques, where a difference in isoelectric points of about 0.01 is sufficient. Additional separation techniques for analysis of multicharged large ions would also be useful. Ion mobility is a technique of great interest as ion mobility resolving power increases proportionally to the square root of ion charge, yielding not only improved peak separation in the mobility cell but in addition, the mobility peak width may provide information about the ion charge state.

An IMS is typically composed of an ionization source, a drift cell, and an ion detector; examples of the latter include a sampling plate, an electron multiplier, or a mass spectrometer. Ion mobility spectrometry separates ions in terms of their mobility with reference to a drift/buffer gas by measuring the equilibrium velocity of the ions. When gaseous ions in the presence of a drift gas experience a constant electric field, they accelerate until a collision occurs with a neutral molecule. This acceleration and collision sequence is repeated continuously. Over time, this scenario averages out over the macroscopic dimensions of the drift tube to a constant ion velocity based upon ion size, charge, and drift gas pressure. The ratio of the velocity of a given ion to the magnitude of the electric field experienced by it is the ion mobility. In other words, the ion drift velocity ($v_d$) is proportional to the electric field strength (E) where the ion mobility $K=v_d/E$ is a function of the ion volume/charge ratio. Thus IMS is a technique similar to mass spectrometry, having a separation component to it. The IMS technique is generally characterized as having high sensitivity with moderate separation power. Separation efficiency is compromised when "bands" of the various ions spread apart as opposed to remaining together in a tight, well-defined beam. This efficiency or resolving power for what is considered "classic" ion mobility (using uniform or quasi-uniform electric field to effect a separation due to the Einstein relationship between mobility coefficient and diffusion coefficient for ions for given ion charge) increases as the square root of applied voltage along mobility cell. This maximum voltage for a given length of mobility cell is restricted by the possibility of glow discharge and decomposition of ions due to heating from rapid velocities in the buffer gas. Increasing the buffer gas pressure does allow application of higher cell voltages and improved mobility resolving power.

Another possible analytical technique, using a new continuous flow technique for separation of gas-phase ions at atmospheric pressure, and referred to as high-field asymmetric waveform ion mobility spectrometry (FAIMS), has recently been described. (see R. W. Purves, R. Guevremont, S. Day, C. W. Pipich, M. S. Matyjaszczyk, *Rev. Sci. Instrum.* 69, 1094-4105 (1998); R. Guevremont, R. W. Purves, *Rev. Sci. Instrum.* 70, 1370-1383 (1999)). This technique is simply a further development of the cylindrical geometry case of the method implemented for the plane geometry and described earlier. (see I. A. Buryakov, E. V. Krylov, E. G. Nazarov, U. K. Rasulev *Int. J. Mass Spectrom. Ion Processes* 128, 143-148 (1993)). Adequate separation capability of this method for isomeric compounds was demonstrated. see D. A. Barnett, B. Ells, R. Guevremont, R. W. Purves "Separation of leucine and isoleucine by elecrtospray ionization-high field asymmetric waveform ion mobility spectrometry-mass spectrometry"; *J.*

*Am. Soc. Mass Spectrom.* 10, 1279-1284 (1999)). This approach is more suitable for coupling with continuous ionization methods such as electrospray. Its main difference from classic ion mobility spectrometry is focusing and recording of only one type of the ions from continuous ion flow for each time moment. All other ions are usually lost. The situation is the same as for all instruments of scanning type which may be adequate when the amount of the sample is not so important or when determination of only one or few known components is necessary. However, use of multi-beam ion pre-selection as proposed in the present invention partially overcomes this drawback and finds general use. Herein we describe the specific embodiment of the modified FAIMS for analysis of aerosol particles.

The combination of an ion mobility spectrometer (IMS) with a mass spectrometer (MS) is well known in the art. In 1961, Barnes et al. were among the first to combine these two separation methods. Such instruments allow for separation and analysis of ions according to both their mobility and their mass, which is often referred to as two dimensional separation or two dimensional analysis. Young et al. realized that an orthogonal time-of-flight mass spectrometer (oTOFMS) is the preferred mass spectrometer type to be used in such a combination because of its ability to detect simultaneously and very rapidly (e.g., with a high scan rate) all masses emerging from the mobility spectrometer. Their combination of a mobility spectrometer with an oTOFMS is herein referred to as an Ion Mobility-oTOFMS or IM-oTOFMS. This instrument comprised means for ion generation, a mobility drift cell, and an oTOFMS with a small orifice for ion transmission coupling the mobility cell to the oTOFMS.

Use of MS as a detector allows for resolution based on mass-to-charge ratio after separation based upon ion mobility. Shoff and Harden pioneered the use of Mobility-MS in a mode similar to tandem mass spectrometry (MS/MS). In this mode, the mobility spectrometer is used to isolate a parent ion and the mass spectrometer is used for the analysis of fragment ions (also called daughter ions) which are produced by fragmentation of the parent ions. Herein, this specific technique of operating a Mobility-MS is referred to as Mobility/MS, or as Mobility/TOF if the mass spectrometer is a TOFMS-type instrument. Other instruments and methods using sequential IMS/MS analysis have been described (see, e.g., McKight, et al. Phys. Rev., 1967, 164, 62; Young, et al., J. Chem. Phys., 1970, 53, 4295; U.S. Pat. Nos. 5,905,258 and 6,323,482 of Clemmer et al.; PCT WO 00/08456 of Guevremont) but none combine the instrumental improvements disclosed presently. When coupled with the soft ionization techniques and the sensitivity improvements realizable through use of the drift cell systems herein disclosed, the IMS/MS systems and the corresponding analytical methods of the present invention offer analytical advantages over the prior art, particularly for the analysis of macromolecular species, such as biomolecules.

The challenging issue when constructing an IMS-MS device is to achieve a high ion transmission from the mobility region into the MS region of the tandem instrument. It is at this interface that the earlier approaches of ion mobility technology using a linear field appear incongruous with the goal of maximizing ion throughput across the IMS/MS interface. The mobility section is operating at a pressure of typically between 1 mTorr and 1000 Torr whereas the MS is typically operating at pressures bellow $10^{-4}$ Torr. In order to maintain this differential pressure it is necessary to restrict the cross section of the opening that permits the ions to transfer from the mobility section to the MS section. Typically this opening cross section is well below 1 mm². Hence it is desirable to focus the ions into a narrow spatial distribution before this interface transmission occurs. Another important property of the ion beam arriving into the MS is the divergence of this beam in the kinetic energy for ion motion in the plane orthogonal to the direction of their insertion into the MS. Ion beam energy divergence is the main factor responsible for the resolution properties of the mass spectra for orthogonal TOFMS. In 2004, Loboda U.S. Pat. No. 6,744,043 described several versions of using of radio frequency (RF) ion guide for focusing of ions inside the mobility cell. However, this approach is suitable for low pressure ion mobility separation not more than a few Torr. Furthermore, RF focusing of ions decreases with increasing of m/z of ions so this method has some important restrictions. As discussed herein, RF focusing of ions in interface region just after the exit orifice of the mobility cell and before the entrance orifice of TOFMS is free from these drawbacks.

H. H. Hill, in the late 1980's, developed methods for introducing large biomolecules from aqueous samples directly into IMS using electrospray ionization techniques. (see Hill, H. H.; and Eatherton, R. L., "Ion Mobility Spectrometry after Chromatography-Accomplishments Goals, Challenges", *J. Research of the National Bureau of Standards, Accuracy in Trace Analysis,* 93(3), 1988, 425; see Shumate, C. B.; and Hill, H. H., "Coronaspray Nebulization and Ionization of Liquid Samples for Ion Mobility Spectrometry", *Analytical Chemistry,* 61, 1989, 601. Recently, Hill and co-workers have interfaced a high resolution atmospheric pressure ion mobility spectrometer to a time-of-flight mass spectrometer and obtained rapid 2-D separations of amphetamines (Steiner, W. E.; Clowers, B. H.; Fuhrer, K.; Gonin, M.; Matz, L. M.; Siems, W. F.; Schultz, A. J.; and Hill, H. H., "Electrospray Ionization with Ambient Pressure Ion mobility Separation and Mass Analysis by Orthogonal Time-of-Flight Mass Spectrometry", *Rapid Commun. Mass Spectrom.,* 15, 2001, 2221-2226), PTH-amino acids (Steiner, W. E.; Clowers, B. H.; Hill, H. H., "Rapid Separation of Phenylthiohydantoin Amino Acids: Ambient Pressure Ion Mobility Mass Spectrometry (IMMS)", *Anal. and Bioanal. Chem.,* accepted October 2002), and chemical warfare degradation products (Steiner, W. E.; Clowers, B. H.; Matz, L. M.; Siems, W. F.; Hill, H. H., "Rapid Screening of Aqueous Chemical Warfare Agent Degradation Products: Ambient Pressure Ion Mobility Mass Spectrometry (IMMS)", *Anal. Chem.,* 2002, 74, 4343-4352). At the interface between the IMS and the TOF, collision-induced dissociation of mobility separated ions can be turned on and off by varying the interface voltage to provide an added dimension of analysis. This and other known approaches for coupling of electrospray ion source with IMS/MS all suffer from large losses of ions in all stages of their transport and some decreases in mobility resolving power due-to significant width of initial ion package formed by interruption (pulse-forming) of the continuous ion flow from the electrospray ion source. The typical sensitivity of these measurements is in the range of μM, which is far worse than that for typical non-IMS electrospray and matrix-assisted laser desorption ionization (MALDI) measurements. MALDI sensitivities in the femto-molar range are typical (a difference of up to nine orders of magnitude). As the continuous electrospray ion source direct is chopped (or pulsed) for introduction of the ion package into mobility cell only approximately 1% of the initial ion source production is utilized in the mobility cell. The relative time width of this ion package to the time between such introductions should be less than the inverse of expected mobility resolving power. Thus, increasing mobility resolving power would lead in this case to additional losses of ions and a further decrease in sensitivity.

This pulse-forming condition is related to that with coupling of continuous ion source with TOFMS before the invention of orthogonal injection of ions into TOFMS. Herein, a method of ion injection into mobility cell is demonstrated which is free from the beam-chopping limitations of usual coaxial introduction of ions.

In 2004, Eriksson U.S. Pat. No. 6,683,302 described an electrospray ion source where heating of droplets emerging from the electrospray capillary under the influence of a strong electric field was provided by microwave energy directed between the spray tip and mass analyzer.

In 2003, Ranasinghe, et al. U.S. Patent Application 2003/0001090 described splitting the liquid flow from a separation device into two approximately equal streams and directing them into two ion spray sources; the first one producing positive ions and the second one producing negative ions. Two TOFMSs were used for recording of these positive and negative ions. In 2004, Van Berkel U.S. Pat. No. 6,677,593 described partial separation of ions in a liquid phase by applying electric or magnetic fields or their combination. Enriched positive ion flow is directed into one capillary whereas the flow with negative ions is sent through another capillary. Due to the large electric field near the tips of the capillaries during operation of the electrospray ion source from solution phases, charge distribution of ions are "spoiled" in the ion formation and extraction process.

In 2004, Berggren, et al. U.S. Pat. No. 6,797,945 described some versions of using piezoelectric formation of charged droplets for electrospray ion source. This approach may be promising for several reasons. ESI coupled with pulsed techniques of ion analysis in classic ion mobility spectrometers is simplified because it is possible to form droplets in controllable short time intervals. It is also appears to be important that droplets may be produced having well known and narrow size distributions. Berggren teaches that it is possible to get ions with less spread in their charges by applying less voltage to the tip of the capillary from where the droplets emerge. However, application of any voltage (to the piezoelectric element located inside investigated solution) may change, to some extent, the conditions for ion formation. Therefore, the charge distribution inside large ions of interest may still be changed from that in the solution at given pH and without additional influences.

An idea to mix microwave voltage for heating with quasi-periodic signal with frequency band 10-10000 kHz for splitting of combustion kernels in internal combustion engine was suggested in 1999 by Gordon, et al. U.S. Pat. No. 5,983,871.

In 2004, Apffel, et al. U.S. Pat. No. 6,797,946 described the nebulizing of solutions and ionization of the neutral species contained in the solutions by atmospheric pressure ionization (API) and atmospheric pressure chemical ionization (APCI) as well as suggesting orthogonal injection of resulting ions into the vacuum part of mass spectrometer. The described version of orthogonal injection of ions may be considered as a further development of the widely used approach for removing of large and low charged droplets from electrospray flow by a gas curtain. Some advantages of this approach may be expected: lower "curtain" gas flow as it is injected in the same direction as electrospray flow, and perhaps, some better sensitivity of measurement and less evaporated solvent flow inside mass spectrometer. However, Apffell nowhere suggests using gas counterflow, ion accumulation in traps, and pulse inserting of ions for analysis which are aspects of the present invention discussed herein.

In 2005, Takats, et al. U.S. Patent Application 2005/0029442 described ion spray from solution using increased speed (more than sound) of nebulizing gas flow assisted with voltage applied to the sample capillary. The experimental data were presented showing very narrow distribution of multicharged ions, sometimes showing reduction to one type of ion. Changes of average ion charge and peak width with applied voltage and the distance from the sample capillary tip to the input heated capillary for inserting ions into mass analyzer for different sample flows were measured. It was shown that ions with relatively low number of charges and low intensity may be detected for zero voltage applied to the sample capillary. The data given for nanoelectrospray for different spray voltages indicate more average charges for the same voltages after some onset voltage below which no ions are detected.

One issued U.S. patent and two pending U.S. patent applications of Schultz et al. (pending U.S. application Ser. No. 10/861,970, filed Jun. 4, 2004; pending U.S. application Ser. No. 11/231,448, filed Sep. 21, 2005; and U.S. Pat. No. 6,989,528) describe a system whereby massive cluster ions or massive cluster ions neubulized in a solvent may be impinged upon a surface both to liberate and ionize surface bound molecules or elements (SIMS) as well as simultaneously providing for nondestructive implantation of a portion of this droplet into the near surface region of a biopolymer which can thereafter be irradiated with a energetic particle source such as a laser (MALDI) for liberation of the molecules within the surface region. These U.S. patent applications are incorporated by reference as though fully described herein). A recently published variant of this approach was called Desorption Electrospray Ionization (DESI) (see Z. Takats, J. M. Wiseman, B. Gologan, R. Graham Cooks; Science Vol. 306, 15 Oct. 2004, pp 471-473). These techniques appears to be a useful tool for the investigation of a variety of surfaces of natural origin including in vivo analyses. The essence of these approaches involves directing the flow of solvent droplets acquired by nebulizer-assisted electrospray to the surface under investigation which is held under usual ambient conditions and insertion of the resulting flow from the surface into a mass spectrometer through an atmospheric pressure interface. Interesting experimental results were demonstrated including the mass spectrum from the finger of a person 50 min after taking 10 mg of the over-the counter antihistamine Loratadine (m/z 383/385). The corresponding peaks are clearly seen in the spectrum. It is stated in the paper that "changes in the solution that is sprayed can be used to selectively ionize particular compounds." However use of high voltage applied to the solvent in the spraying capillary would change the conditions for formation of ions from the sample compared to those for initial solvent. Thus, for example, the control of pH in the solvent for producing of ions with corresponding charge distribution is impossible in this case as is the case for a typical electrospray ion source. A method free from this drawback is an aspect of the present invention.

Attempts to perform fast three dimensional separation of ions are also known. In 2001, Clemmer, et al. U.S. Pat. No. 6,323,482 described an approach whereby a quadrupole mass filter is located between mobility cell and time-of-flight instrument and is used for separation of non-resolved mobility peaks for providing collision-induced dissociation for selected ions. In 2003, also Clemmer U.S. Pat. No. 6,559,441 suggested the performance of two consecutive separations of ions before mass analysis due to two different molecular characteristics.

In 2004, Woods and Virgil, in U.S. Pat. No. 6,797,482, described the approach for high-resolution identification of solvent-accessible amide hydrogens in protein binding sites. Exchange in solution of "open" hydrogen atoms for heavy hydrogen atoms—tritium and deuterium—is used. Therefore, hydrogen atoms buried inside folded proteins are not exchanged. To reveal the corresponding amino acid residues with substituted and non-substituted H-atoms, proteolysis by special enzymes working under low temperature (close to 0° C.) and in strong acidic conditions (for pH about 2, 7) is used. Such low pH values and low temperatures significantly suppress isotopic exchange of H-atoms so it is possible to conserve information about initial structure of the protein in solution. Further HPLC separation is performed in such severe conditions for the same reason. The number of substituted H-atoms in different fractions is estimated by scintillator counting for the case of tritium exchange and mass spectrometry measurements for the case of deuterium exchange. The '482 patent gives a detailed overview of this field. It teaches that using mass spectrometry for solving these problems is restricted to overall determination of the number of substituted H-atoms for corresponding ions without further attempts to locate the sites having these atoms. Using the approach described therein, it is difficult to find locations of substituted H-atoms very precisely.

All of the above-referenced U.S. patents and published U.S. patent applications are incorporated by reference as though fully described herein.

Although much of the prior art resulted in improvements in ion production, focusing, separation, and in ion throughput from ion source to the mobility cell and to the mass spectrometer in tandem instruments, there is room for additional improvement in all these directions. The inventors describe herein a concept and designs of a new type electrospray ion source, multi-beam ion mobility and mass separations with multi-channel data recording which result in instrumental embodiments to provide improved ion production from investigated samples, their separation and measurements.

BRIEF SUMMARY OF THE INVENTION

The present invention is directed instrumentation and methodology for the characterization of chemical samples in solutions or on a surface which is based on modified ionization methods with or without adjustable pH and controllable H-D exchange in solution, an improved ion mobility spectrometer (IMS), a multi-beam ion pre-selection of the initial flow, and coordinated mobility and mass ion separation and detection using a single or several independent time-of-flight mass spectrometers for different beams with methods for fragmenting ion mobility-separated ions and multi-channel data recording.

In one aspect of the present invention, there is an apparatus for analyzing a sample, the apparatus comprising a source for the generation of a flow of gaseous ions or a mixture of gaseous ions and gaseous neutral species from the sample, the source producing the flow in a first direction; an orthogonal collection region fluidly coupled to the source; and, at least one ion mobility assembly fluidly coupled to the source, the ion mobility assembly comprising a plurality of mobility tubes, wherein the ion mobility assembly has a separation axis which is orthogonal to the first direction.

In some embodiments, the ion mobility assembly further comprises a plurality of CID tubes and a plurality of exit tubes, the CID tubes being fluidly coupled to the mobility tubes and the exit tubes being fluidly coupled to the CID tubes. In some cases, the ion mobility assembly further comprises at least one multichannel RF interface fluidly coupled to at least one of the CID tubes. In some embodiments, the at least one multichannel RF interface comprises pairs of rods and confining plates. The ion mobility assembly may further comprise at least one multichannel RF interface fluidly coupled to at least one of the mobility tubes. In some embodiments, the at least one multichannel RF interface comprises pairs of rods and confining plates. In some embodiments, the apparatus further comprises at least one TOFMS fluidly coupled to the ion mobility assembly. In some embodiments, the TOFMS comprises a position sensitive detector. The at least one TOFMS may be an oTOFMS. The at least one TOFMS may be a LoTOFMS. In some cases. the TOFMS may comprise a detector comprising a plurality of anodes in which two or more anodes of the plurality are each linked to single detector channels. In such cases, the single detector channel is a TDC channel. In some embodiments of the apparatus, the orthogonal collection region comprises one or more voltage grids. In some embodiments, the apparatus further comprises an ion trapping region fluidly coupled to the orthogonal collection region and to the ion mobility assembly, the ion trapping region comprising at least one ion trap. The ion traps may be DC field traps. The ion traps may be RF voltage traps. In some embodiments having an ion trapping region, the ion trapping region comprises a variable size exit orifice. In some embodiments, the apparatus further comprises a laser positioned to excite the gaseous ions or mixture of gaseous ions and gaseous neutral species in the ion trapping region, in the orthogonal collection region, or in both the ion trapping region and in the orthogonal collection region. In some embodiments, the apparatus further comprises means for a variable gas flow in the source, or in a region between the source and the ion mobility assembly, or in both. In some embodiments, the apparatus further comprises one or more mirrors in the region between the source and the ion mobility assembly In some embodiments, the apparatus further comprises a laser positioned to excite the gaseous ions or mixture of gaseous ions and gaseous neutral species in the orthogonal collection region. In some embodiments, the orthogonal collection region comprises at least one voltage grid for each mobility tube In some embodiments, the source is selected from the group consisting of a laser desorption source, a cluster bombardment source, a secondary ion source, a desorption electrospray ionization source an electrospray ionization source, photoionization source, and any combination thereof. Preferably where a laser desorption source is used, it is a matrix assisted laser desorption ionization source. In some cases, the source comprises a droplet generator and is selected from the group consisting of electrospray source, a pneumo-spray source, an atmospheric pressure ionization source, a laserspray source, a vibrating orifice aerosol generator, and any combination thereof. In some embodiments, the apparatus further comprises means for a variable gas flow in one or more components of the ion mobility assembly. In some embodiments, the apparatus further comprises at least one funnel, the at least one funnel comprising electrode structures providing variable high and low electric fields, the at least one funnel positioned immediately before the at least one mobility tube. In some embodiments wherein the apparatus further comprises at least one funnel comprising electrode structures providing variable high and low electric fields, the variable high and low electric fields comprise spatially alternating high and low electric fields. In some embodiments wherein the apparatus further comprises at least one funnel, the apparatus further comprising means for a variable gas flow in the at least one funnel. In some embodiments the apparatus further comprises at least one funnel, the at least one funnel comprising electrode structures providing variable high and low electric fields; at least one capillary electrode assembly; or, both the at least one funnel and the at least one capillary electrode assembly, wherein the at least one funnel and the at least on capillary electrode assembly are positioned at the exit of, or immediately after the at least one mobility tube. In some embodiments of the apparatus, the plurality of mobility tubes comprise electrode configurations producing periodic electric fields, hyperbolic electric fields or a combination of periodic and hyperbolic electric fields. In some embodiments of the apparatus, one or more of the plurality of mobility tubes comprises an entrance cone electrode. In some embodiments of the apparatus, the at least one ion mobility assembly comprises a plurality of ion mobility assemblies and wherein the plurality comprises at least one pair of ion mobility assemblies and wherein one ion mobility assembly of the pair is opposed to the other ion mobility assembly of the pair. In some embodiments of the apparatus, the source further comprises means to deliver a pH adjustor composition to the sample. In some embodiments of the apparatus, the apparatus further comprises a pH measuring device positioned in the source. In some embodiments of the apparatus, the source further comprises means to deliver a deuterated composition to the sample. In some embodiments, the apparatus further comprises a microwave voltage source coupled to the source. In some embodiments, the apparatus further comprises a sound frequency voltage source coupled to the source. In some embodiments of the apparatus, the source comprises an aerosol sampler, the aerosol sampler comprising a capillary and a chamber containing a radioactive element, the chamber operable to hold opposite charges near opposing walls of the chamber.

In another aspect of the present invention, there is a method of analyzing a sample comprising the steps of creating a flow of gaseous ions or a mixture of gaseous ions and gaseous neutral species from the sample; directing the flow into an orthogonal collection region; orthogonally injecting the flow from the orthogonal collection region into at least one ion mobility assembly, the at least one ion mobility assembly comprising a plurality of mobility tubes; and, detecting the flow exiting the ion mobility assembly.

In some embodiments of the method, the ion mobility assembly further comprises a plurality of CID tubes and a plurality of exit tubes. In some embodiments of the method, the ion mobility assembly further comprises at least one multi-channel RF interface. In some embodiments of the method, the ion mobility assembly further comprises at least one multi-channel RF interface. In some embodiments of the method, the step of detecting comprises detecting with at least one TOFMS, the TOFMS comprising a position sensitive detector. In some cases, the TOFMS is an oTOFMS. In some cases, the TOFMS is a LoTOFMS In some embodiments of the method, the step of detecting comprises detecting with at least one TOFMS comprises detecting with at least one TOFMS comprising a detector comprising a plurality of anodes in which two or more anodes of the plurality are each linked to single detector channels. In some cases wherein the TOFMS comprises a detector comprising a plurality of anodes in which two or more anodes of the plurality are each linked to single detector channels, the single detector channel is a TDC channel. In some cases, the step of directing the flow into an orthogonal collection region comprises directing the flow near or through one or more voltage grids. In some embodiments of the method, the method further comprises the step of directing the flow of gaseous ions or mixture of gaseous ions and gaseous neutral species through an ion trapping region comprising at least one ion trap, the ion trapping region being located between the orthogonal collection region and the ion mobility assembly. The ion traps may be DC field traps, RF voltage traps or a combination thereof. In some embodiments involving an ion trapping region, the step of directing the flow into the ion trapping region comprises directing the flow through a variable size exit orifice. In some embodiments involving an ion trapping region, the method further comprises the step of irradiating the flow of gaseous ions or mixture of gaseous ions and gaseous neutral species with a laser, the step of irradiating being preformed in the ion trapping region, in the orthogonal collection region, or in both the ion trapping region and the orthogonal collection region. In some embodiments, the method, further comprises the step of applying a variable gas flow to the flow of gaseous ions or mixture of gaseous ions and gaseous neutral species during the steps of creating, orthogonally injecting, or during both the steps of creating and orthogonally injecting. In some cases, the method further comprises the step of directing the flow of gaseous ions or mixture of gaseous ions and gaseous neutral species through one or more mirrors during the steps of creating, orthogonally injecting, or during both the steps of creating and orthogonally injecting. In some embodiments of the method, the step of creating comprises creating with a source selected from the group consisting of a laser desorption source, a cluster bombardment source, a secondary ion source, a desorption electrospray ionization source an electrospray ionization source, photoionization source, and any combination thereof. Preferably, in cases using a laser desorption source, the laser desorption source is a matrix assisted laser desorption ionization source. In some cases, the step of creating comprises creating droplets with a source selected from the group consisting of an electrospray source, a pneumo-spray source, an atmospheric pressure ionization source, a laserspray source, a vibrating orifice aerosol generator, and any combination thereof. In some embodiments wherein droplets are created, the method further comprises the step of splitting the droplets into positively and negatively charged droplets by quasi-resonant sound electric field or ultrasound frequency electric field. In some embodiments wherein droplets are created, the method further comprises the step of drying the droplets by ambient gas heating and microwave absorption. In some embodiments of the method, the method further comprises the step of applying and varying a gas flow in one or more components of the ion mobility assembly. In some embodiments of the method, the method further comprises the step of directing the flow through at least one funnel, the funnel positioned immediately before the at least one mobility tube, the at least one funnel comprising electrode structures providing variable and/or spatially alternating high and low electric fields. In some embodiments of the method described in the preceding sentence, the method, the method further comprises varying a flow of gas in the at least one funnel; varying polarity and/or magnitude of voltage across the funnels; or, varying both the flow of gas and the polarity and/or magnitude of voltage. In some embodiments of the method, the method further comprises the step of irradiating the flow of gaseous ions or mixture of gaseous ions and gaseous neutral species with laser radiation, the step of irradiating being preformed before the step of directing the flow into the orthogonal collection region. In some embodiments of the method which comprises irradiation of the flow with laser radiation, the method further comprises the step of varying a flow of gas during the step of creating the flow of gaseous ions and neutral species. In some embodiments of the method using a step of laser irradiating, the step of irradiating comprises reflecting the laser radiation from one or more mirrors In some embodiments of the method, the method further comprises the step of applying periodic electric fields, hyperbolic electric fields of a combination of periodic and hyperbolic electric fields in one or more of the plurality of mobility tubes. In some embodiments of the method, one or more of the plurality of mobility tubes comprises an entrance cone electrode. In some embodiments of the method, the step of orthogonally injecting the flow into the at least one ion mobility assembly comprises orthogonally injecting the flow into a plurality of ion mobility assemblies and wherein the plurality comprises at least one pair of ion mobility assemblies wherein one ion mobility assembly of the pair is opposed to the other ion mobility assembly of the pair In some embodiments of the method, the method further comprises the step of delivering a pH adjustor composition to the sample. In some embodiments of the method wherein a pH adjustor composition is delivered, the step of delivering a pH adjustor comprises mixing the sample with flows of acid or base buffers or a combination of acid and base buffers. In some embodiments of the method wherein a pH adjustor composition is delivered, the step of delivering is regulated by a feedback signal. The feedback signal may be generated by a pH measuring device. In some embodiments of the method wherein a pH adjustor composition is delivered, the step of detecting comprises detecting for samples at specific pH values. In some embodiments of the method, the method further comprises the step of delivering a deuterated composition to the sample. In some embodiments of the method, the method further comprises the step of applying a microwave voltage to the flow of gaseous ions or mixture of gaseous ions and gaseous neutral species. In some embodiments of the method, the method further comprises the step of applying a sound frequency voltage to the flow of gaseous ions or mixture of gaseous ions and gaseous neutral species. In some embodiments of the method, the method further comprises the step of collecting intensity data and correlating the intensity data from positive and negative ions to identify positive ion/negative ion pairs, wherein the intensity data is acquired from the step of detecting. In some embodiments of the method, the method further comprises the step of collecting intensity data and correlating intensity data with the ion charge distribution of the sample, wherein the intensity data is acquired from the step of detecting. In some embodiments of the method, the step of creating further comprises generating an aerosol. In some embodiments of the method involving creation of an aerosol, the step of creating the flow of gaseous ions or mixture of gaseous ions and gaseous neutral species from the sample comprises creating the flow from an aerosol. In some embodiments of the method, the sample comprises a biological sample comprising non-exchangeable isotopically-labeled and non-isotopically-labeled chemical species and the method further comprises using shifts in mass-to-charge ratio related to the isotopic labeling to analyze the biological sample. In some embodiments of the method described in the preceding sentence, the chemical species is a drug. In another embodiment of the method comprising the use of non-exchangeable isotopically-labeled and non-isotopically-labeled chemical species, the chemical species is a known mixture of isotopically-labeled and unlabeled chemical species and the method further comprises correlating the shifts in mass-to-charge ratio to determine the mass of a chemical complex comprising the chemical species and one or more other unknown chemical species; and, the mass of the one or more other unknown chemical species.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 11. Schematic view of specific part of interface for investigation of aerosol particles.

DETAILED DESCRIPTION OF THE INVENTION

Figure 1A:
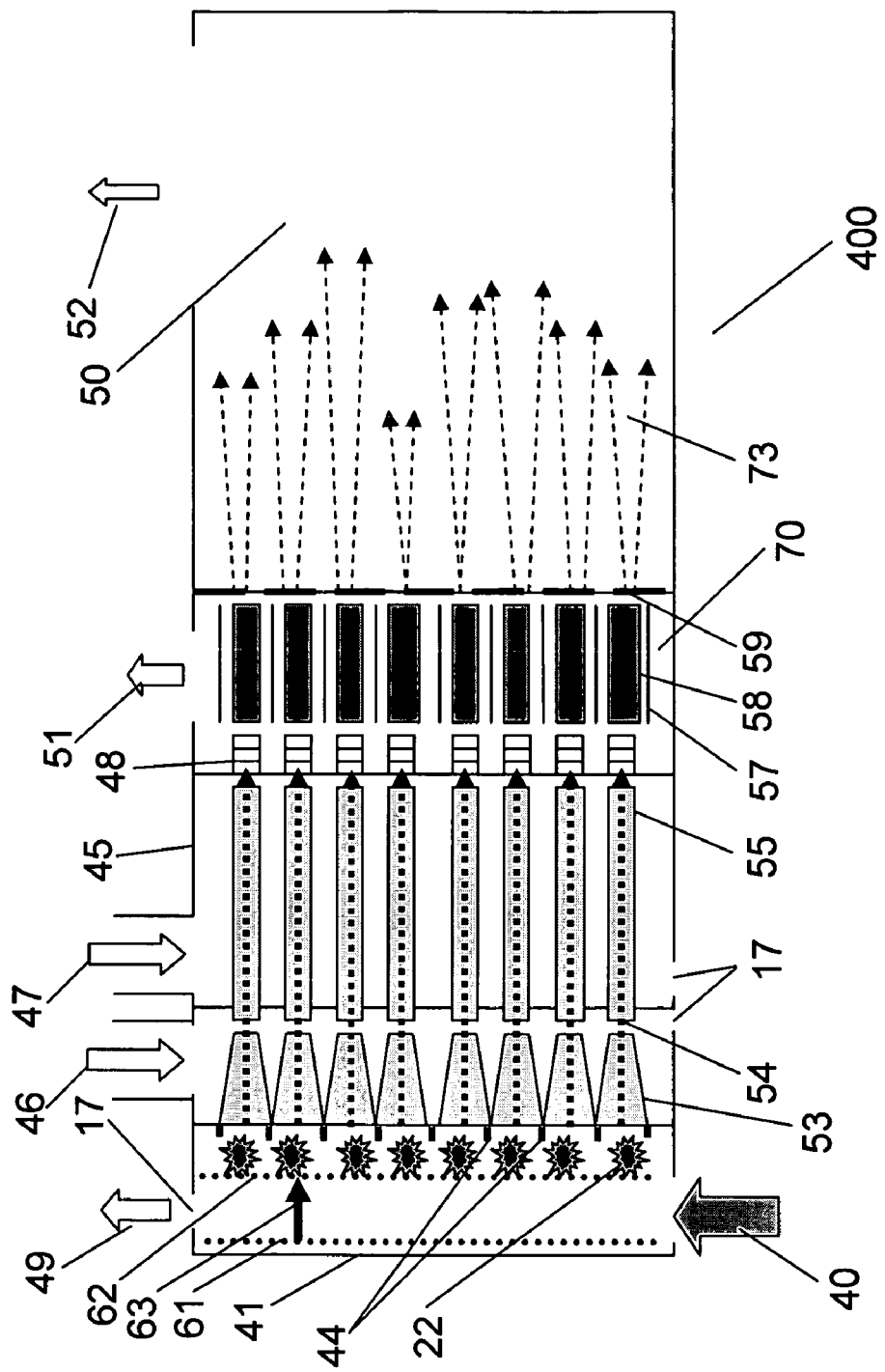
FIG. 1A. Schematic of a measuring unit for multi-beam ion mobility drift cell TOFMS with multi-channel data recording, common for most embodiments of the invention.

As used herein, "a" or "an" means one or more, unless otherwise expressly indicated or obvious from the context. This is particularly true when reference is made to instrumental apparatuses or individual components of the same.

As used herein, a "plurality" means two or more.

As used herein, "IM" is defined as ion mobility. As used herein, "IMS" is defined as "ion mobility spectrometry" when used in the context of a technique or "ion mobility spectrometer" when used in the context of an instrument or apparatus.

As used herein, a "zwitterion" is a molecule with one ore more positively and one or more negatively charged structural groups in which the total positive charge is equal to the total negative charge. Thus the total charge of zwitterion is zero. The "isoelectric point" is the pH value (pI) at which the average electric charge is zero on the molecule.

A charged zwitterion may be a zwitterion with one or more excess positive or negative charges. For example, at some pH bradykinin can exist as a zwitterion which is charged during a MALDI desorption as $MH^+$.

As used herein, a "mobility cell assembly" is defined as a single or multi-channel device which performs mobility separation of ions and comprises at least one mobility tube, a collision induced dissociation (CID) tube wherein collision-induced ionization occurs, and optionally, final ion transport with cooling gas flow through "exit tubes" into multi-channel RF-ion guide. In the multi-channel embodiment, the mobility cell assembly comprises a plurality of first mobility tubes, CID tubes, exit tubes and RF-ion guides, preferably with each of the aforementioned component in series with one another and each series in parallel with at least one other series. Multi-bore and Multichannel are used interchangeably.

As used herein, "mobility tube" is an ion mobility cell; the terms ion mobility cell and mobility tube are synonymous herein. The term "exit tube" is defined as the final mobility tube in a series of mobility tubes.

As used herein, the term "funnel", when used in reference is defined as a conical device comprising electrode pairs (of descending open area along the direction from the ion source to the ion detector) to which attractive or repulsive voltages may be applied linearly or to individual electrodes. The funnel may optionally contain an exit tube comprising a capillary exit end formed by alternating electrode pairs.

As used herein "collision induced dissociation tube" or "CID tube" is a mobility tube assembly which may also contain a funnel electrode assembly and a capillary exit tube electrode assembly in which high electric fields may be created sufficient either to further focus ions onto the axis of the mobility tube or, at higher voltages, to provide collision-induced dissociation of ions into structural fragments.

As used herein, an "orthogonal collection region" is defined by the volume between at least one electrode and/or voltage grid pair through which ions (possibly of both signs) and neutrals which are mixed with a carrier gas pass orthogonally in front of the entrance of at least one IM tube. Neutrals which are formed within the gas flow through this region are transformed into ions by an ionization or fragmentation process (such as by a laser) within this region. This region may also be referred to as an "orthogonal IM injection region".

As used herein, an "orthogonal collection region" is defined by the volume between at least one electrode and/or voltage grid pair through which ions (possibly of both signs) and neutrals which are mixed with a carrier gas pass orthogonally in front of the entrance of at least one IM tube. Neutrals which are formed within the gas flow through this region are transformed into ions by an ionization or fragmentation process (such as by a laser) within this region. This region may also be referred to as an "orthogonal IM injection region".

As used herein, an "orthogonal collection region" is defined by the volume between at least one electrode and/or voltage grid pair through which ions (possibly of both signs) and neutrals which are mixed with a carrier gas pass orthogonally in front of the entrance of at least one IM tube. Neutrals which are formed within the gas flow through this region are transformed into ions by an ionization or fragmentation process (such as by a laser) within this region. This region may also be referred to as an "orthogonal IM injection region".

As used herein, the term "separation axis" as it relates to an ion mobility assembly or any individual component of an ion mobility assembly is the axis defining the direction of travel of ions and/or neutral species traversing or being transported through the ion mobility assembly or any individual component of the ion mobility assembly.

As used herein. IM-oTOFMS refers to a combination of an ion mobility spectrometer with an orthogonal time of flight mass spectrometer. An IM-TOFMS more generally refers to a combination of an ion mobility spectrometer with a time of flight mass spectrometer.

As used herein the term "DESI" refers to desorption electrospray ionization.

The present invention is mainly directed to a system and methods consisting of an ion mobility drift cell transporting ions in a gas at high pressures from any ion source (e.g., a MALDI (matrix assisted laser desorption ionization) or other laser desorption source, a cluster bombardment source, a secondary ion source, a desorption electrospray ionization source an electrospray ionization source, photoionization source, or any combination of the foregoing) into a mass spectrometer. FIG. 1A shows a schematic of an embodiment of a combined multichannel IM-TOFMS analyzer assembly (400). The multichannel IM-TOFMS analyzer assembly (400) comprises an ion mobility assembly and an orthogonal TOFMS. The various components of the ion mobility assembly have entrance and exit openings to allow beams of ions an/or beams of ions and neutrals to enter and exit. The use of static nonlinear periodic fields (see U.S. Pat. Nos. 6,639,213; 6,897,437; and 6,992,284 to Schultz et al., incorporated by reference as though fully described herein) to funnel ions from a large area (even at moderately high pressures—including atmospheric pressure) into a small bore multichannel ion mobility cell and still retain high mobility resolution is the counterintuitive concept which is an aspect of the present invention. The electrode configurations of mobility cells capable of producing periodic fields, hyperbolic fields and combinations of periodic and hyperbolic fields are now known in the art through the aforementioned patent references. By use of an electrostatic funneling of the ions at the beginning of the IM cell, a large volume of ions is collected and compressed and passed into a subsequent smaller bore section of the mobility cell. Such an arrangement can still maintain an overall high mobility resolution after transport through the entire mobility cell. This is because the funnels (53) can be constructed of electrode structures which provide a spatially alternating high and low field which acts to focus and randomize the ion path lengths in the funnel (and in subsequent smaller bore sections of the mobility cell). This even works at pressures near atmospheric pressure. Thus ions near the entrance edges of the funnels are mixed with ions which enter near the center region of the funnels and the result is that all the ions irrespective of where they enter the entrance funnel experience the same randomized path length through the funnels. Furthermore, by making the length of the funnel (53) small compared to the length of the IM tube (55), the effect of unequal path lengths can be further minimized. The exit end of the IM tube may also contain a funnel and/or capillary electrode assembly to further reduce the size of the ion beam, reduce gas flow into and increase the efficiency of pumping out of the interface region (70). By placing numerous such multi-bore IM-TOFMS assemblies (400) opposite one another (see FIG. 1B), one may construct opposing multi-bore arrays of IM cells whereby oppositely charged ions can be extracted from a long column of ions mixed with a near atmospheric pressure gas flow (40) which is orthogonal to the axes of the mobility cell arrays. Pumping (49) provides the gas flow inside the orthogonal collection region (41). It is thus possible to collect ions from a large rectangular or cylindrical volume (41) of ions or post-ionized atoms or molecules entrained in a gas flow which is orthogonal to the axis of the multi-bore IM cell or of one or more opposed multi-bore cell arrays. By intermittently applying voltages on grids (61) and (62) (which may be independent pairs of grids individually biased in front of each funnel (53)), it is possible to create a field (63) which moves ions (22) orthogonal to the direction of ion/gas flow motion to the entrances of the funnels (53) restricted by collimating electrodes (44). The entrained ions are thus forced to deviate orthogonally from the gas stream and into the IM arrays, effecting orthogonal injection into the IM arrays (see FIG. 1A). The injection is said to be orthogonal because the path of travel in the IM arrays is orthogonal to the path of travel in the preceding gas train. The manipulation and further insertion of the ions (22) can be achieved by controlling the polarity and/or magnitude of voltages across the funnels (53), the IM tubes (55) and by the independent gas flows (46) and (47) into the funnels (53) and the section (45) of IM tubes (55) using variable gas pressures and control of flows through variable pumping orifices (17). Thus the gas flow can be out of the funnel into the orthogonal collection region (41) or the flow can be reversed so that some gas comes into the funnel from the orthogonal collection regions (41) as desired. The type of gas introduced (46) can also be different in the funnel (53)(e.g., Xe) from the gases in the source beam (40) (e.g. atmosphere or He) and the gases introduced (47) (e.g., He) into the IM section (45). Thus IM spectra acquisition from a nearly continuous source of ions is possible (or from a continuous stream of neutrals which are periodically ionized by, for example, a line focused pulsed laser). After exiting the IM channels through relatively small apertures or capillary tube electrodes (48), ions enter the interface region (70) which is at a lower gas pressure than the IM channels. This is achieved by differential pumping (51). DC voltages are applied to rings of CID tubes (the exit tube portion of which may also be a funnel and capillary tube electrodes) (48) to prevent ions from diverging from the axis by the gas flow. The main function of the CID tubes is to collect ions coming from corresponding IM channels and transport them to the multi-channel RF ion guide (70). However, high electric field inside CID tubes may optionally be applied to provide collision induced dissociation of some chosen ions. The CID and exit tube (48) is shown in FIG. 1A for illustration purposes as a separate unit which is detached from the IM tube (55); however, the entire continuous assembly may contain an IM tube, CID tube and funnel exit tube which comprise one entire continuous assembly. Furthermore, the exit tube may contain a capillary structure comprising biased electrode pairs which also provides the formation of a supersonic gas expansion of IM carrier gas containing analyte ions into the RF interface region (70). To focus each ion beam (54), a multi-channel RF-ion guide (70) is used. This ion guide shown in detail in the top part of FIG. 6 consists of pairs of rods (58) and confining plates (57) between each pair. RF-voltage of the same phase is applied to rods. DC voltages of rods and confining plates are the same. The voltage difference between the confining plates and the TOFMS (50) is adjusted to give ions the energy they need to enter the TOFMS and to be detected (determined by TOFMS geometry). These plates allow ion confinement (59) between rods. Ions (73) entering the orthogonal TOFMS (50) have some divergence and different velocities. Due to RF-focusing and cooling they are entering the TOFMS through small orifices fairly below 1 mm diameter, thus a single pump (52) is sufficient for good operating pressure. In the instant apparatus, the ion mobility assembly may comprise at least one mobility tube only. Alternatively, it may comprise at least one mobility tube and at least one CID tube and at least one exit tube, and optionally, at least one multichannel RF interface. Alternatively, it may comprise at least one mobility tube and at least one multichannel RF interface. The TOFMS is preferably an oTOFMS.

Simultaneous Orthogonal Insertion of Ions From the Gas Stream (40) Into Opposed Parallel Channel IM Mobility Arrays (FIG. 1B) and the Addition of Trapping Regions (21, 22) Between the Orthogonal Accumulation Region (41) and the Entrance of the Funnels (53)

Figure 1B:
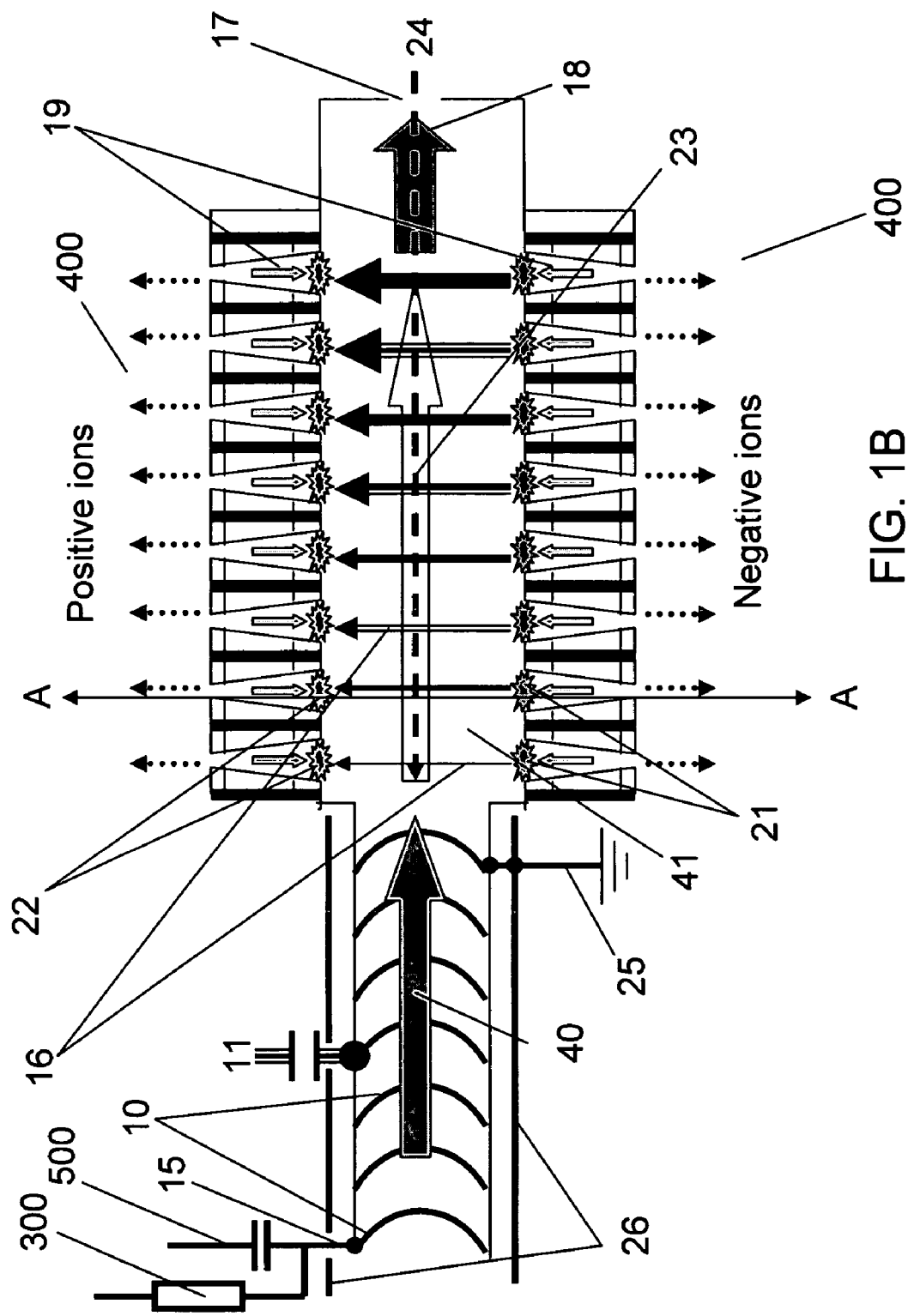
FIG. 1B. Schematic view of ion and neutral trapping, postionization and orthogonal IM injection region common for different embodiments of the present invention.

Two (or four) multichannel ion mobility oTOFMS measuring units (400) may be opposed as, for example, shown in FIG. 1B. "Opposed" in this sense includes, for example, "vertically opposed", "horizontally opposed", "diagonally opposed", etc.; all that is required is that the opposing measuring units are configured 180° with respect to one another. FIG. 1B shows a pair of ion mobility assemblies in which each assembly of the pair is opposed to the other assembly of the pair. In addition to this difference from FIG. 1A we also incorporate the capability to use variable electric fields (16) of increasing strength from the left to the right orthogonal to the direction of ion (or droplet) motion within the trapping region provide. These variable fields can provide some mobility size selection of ions as they are directly injected into the entrance funnels or alternatively as they are introduced into specific trapping regions in front of the funnels. Since the ions of smaller cross-section can be easily deflected from the from gas flow (40) this leaves only the ions of successively larger cross-sections remaining in the gas flow and these heavier ions will subsequently appear before the entrance of successive funnels (from left to right in FIG. 1B). Here positive ions are directed to the traps (22) (in the top of FIG. 1B) when they are under an electric field (16) force, (which is higher than the force from the gas counter flow (19) coming from the multichannel mobility cells). The corresponding negative ions will be trapped in traps (21) shown in the bottom half of FIG. 1B. As a result, the increments with which the electric field is increased from the first trap (close to the entrance of the orthogonal IM injection region) to the next should be chosen such as to provide close to uniform ion density over the traps for a given type of samples. Once trapped in front of the IM channels, ions are introduced inside cell channels either by a pulsed increase of each of the fields (16) or, this insertion process may be further assisted, by additional pulsed electric fields applied across the entrance cone of each mobility channel. The amplitude of the field (16) varies for each trap and is adjusted to force ions of a certain size range into an IM channel (increasing ion sizes from the first trap to the next ones). (It should also be understood that some modified form of the grids (61) and (62) shown in FIG. 1A might be added to aid in localizing and injecting the ions into the funnels). The time that ions spend in the orthogonal IM injection region (including optional ion trapping) should be slightly longer than the time they spend in the mobility cell. Thus the next portion of ions will not be mixed with the previous one and very few of the ions from the continuous source will be lost. The gas pressure inside the interface between the ion source and the mobility array trapping regions may be about 100 Torr. Then the gas pressure inside mobility cells may be close to 150 Torr. Such pressure is sufficient to obtain relatively high mobility resolution (about 100 even for singly charged ions). Computer simulations suggest that it is possible to effectively focus ions at such pressure. This pressure in the mobility cell is suitable for providing the TOFMS operation. The velocity of the gas flow (18) along the axis of the trapping region should be such that the distance traveled by the gas during the time that ions spend in the orthogonal IM injection region is slightly longer than the length of the orthogonal IM injection region (for estimations, we used about 5 cm). It may be done by choosing an appropriate "size" for the exit orifice (17) at the end of the trapping region. This may be a physical orifice with variable size or it may be the orifice interior to a flow controller or variable leak valve whose size can be varied. After introducing trapped ions inside the IM channels the electric fields (16) moving ions into the traps are switched to zero. The fields are switched on in orthogonal direction. A laser pulse (24) for decomposing neutral zwitterions located on the axis of the trapping region (23) is applied. The apparatus in FIG. 1A can also be used at higher pressures near or above atmosphere as no RF trapping in front of each entrance (21, 22) is used. The counter gas flow (19) from each mobility cell may be made extremely weak by appropriate manipulation of the size of the exit orifices (17) and the speed of pumping after the exit orifices (17). The orthogonal region between the opposed multi-bore arrays is then filled with ions and neutrals. After some filling time which is ideally similar to the transit time of the ions through the multi-bore mobility assemblies, the electric fields (16) are applied to extract ions from the orthogonal stream into the nearest mobility cell array. After the ions are removed from the region and have entered the mobility cell assemblies, an energetic ionization source (24) (which may be a laser) is applied to the center region of the mobility cell to either ionize neutrals or to create ions from preformed neutral zwitterions.

Figure 4:
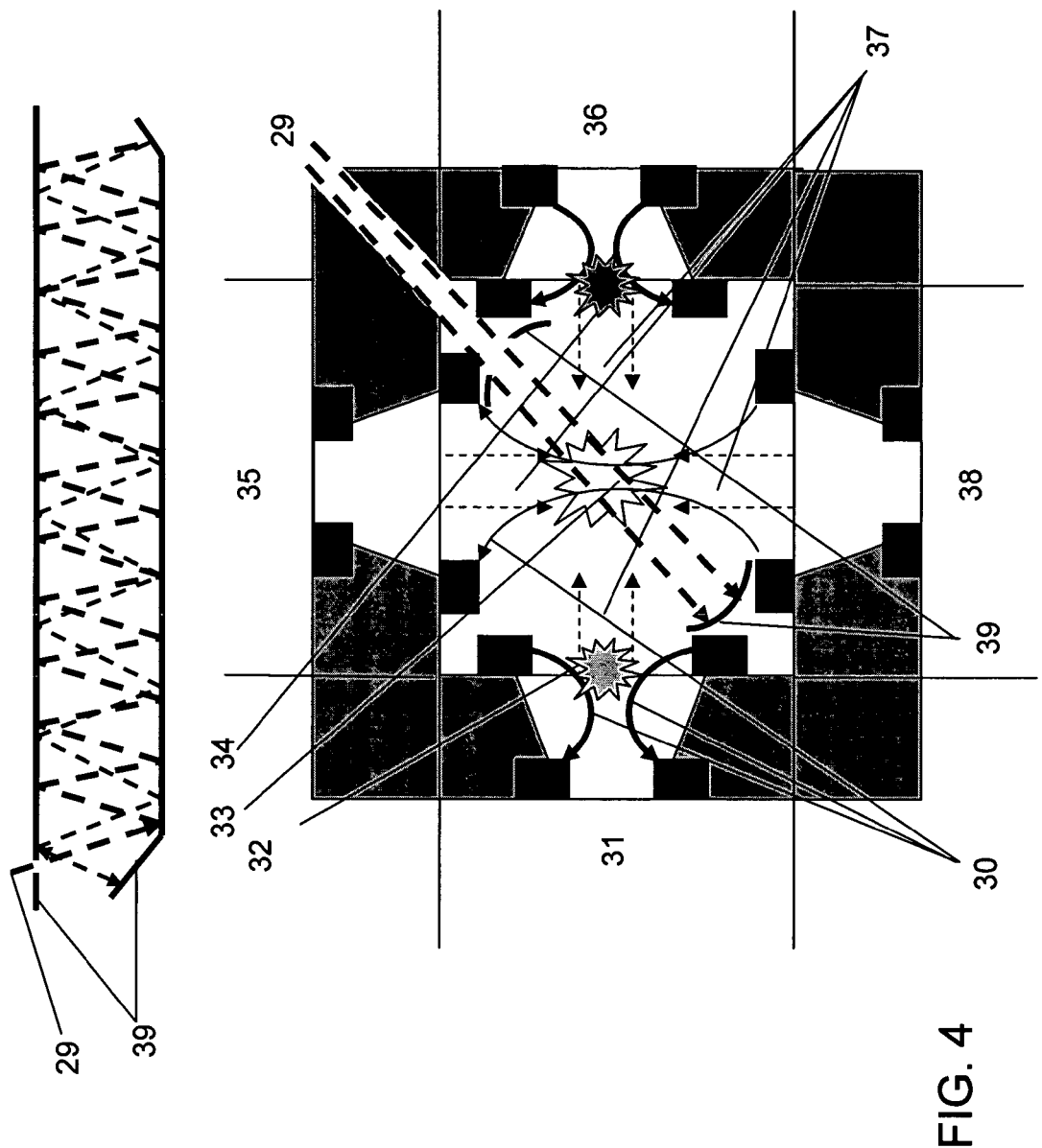
FIG. 4. Section A-A from FIG. 1B and FIG. 2. Neutrals are trapped in the center, positive ions are trapped to the left, and negative ions to the right.

In case this arrangement of the laser beam (24) (along axis of the gas flow) is not suitable (as it can, in some cases, produce undesirable ions in the region of initial flow from the sample (40)), it is possible to arrange the laser beam in the orthogonal direction (29) shown in FIG. 4 (view from section A-A of FIG. 1B). Using two mirrors (39) shown in the top of FIG. 4 allows multiple passing by the laser beam the region of desired ion production. The zwitterions and other neutral species (33) are focused along the axis of the trapping region by counter gas flows (37) from the four multi-channel mobility cells (400) located at positions (31), (35), (36) and (38) as shown in FIG. 4. The electric fields at the entrance of the mobility cell channels (30) for trapping and inserting of positive (32), negative (34) initial ions and ions from zwitterions are also shown. Under increasing electric field, the positive and negative ions formed from zwitterions in (33) travel to the top and the bottom mobility cells, respectively. Other neutral molecules in (33) do not form ions if the photon energy in laser pulse (somewhat more than 2 eV, far below the ionization potential of most chemical substances) is only sufficient to fragment zwitterions and separate complimentary positive and negative ions.

The additional features of the invention are (i) controllable variation of the solution pH to form zwitterions and/or the controlled variations of the concentration of $D_2O$ or some other deuterated substance for providing H-D exchange in solution, (ii) extraction of both positive and negative ions, followed by selective fragmentation of zwitterions at a given pH to create simultaneously (and in co-incidence) oppositely charged fragments from the neutral zwitterion, (iii) ion and neutral pre-selection by flow characteristics of the molecular movement in the gas flow prior to formation and injection of the ions into the multi-bore or opposing multi-bore IM structures (iv) coordinated mobility and mass ion separation and detection using a single or several independent TOFMS (for different beams) with on demand and controllable fragmentation (e.g., collision-induced dissociation (CID) or photo-ionization/fragmentation, or photofragmentation) of selected ions without losing other ions for analysis, and (v) multi-channel data recording. These implementations aim at making a more efficient use of sample and obtaining maximum useful possible information about the sample in a reasonably short time. Specifically, the improvements lie in providing a three-dimensional separation of the solution constituents based on (i) charge balance in the biomolecule at the isoelectric point pI (at the corresponding pH=pI, the average charge of the molecule is 0), (ii) ion mobility separation, and (iii) mass analysis. Additional information about ions or even additional separation may be supplied by controllable H-D exchange in solution since the shifts in isoelectric points for differently deuterated biomolecules of the same biopolymer may be different in the presence of deuterated solvent molecules. Higher sensitivity and more effective sample use are achieved by maximizing ion production and extraction (preferably both negative and positive) from the sample. This includes accumulation and decomposition of zwitterions, multiple ion beam trapping, high transmission orthogonal injection into a high gas pressure mobility cells, high transmission mobility cell/TOFMS interface comprising original multi-channel RF-ion guide. To reduce the acquisition time and the sample consumption, a special procedure will be used to predict the isolectric point of a given biopolymer from the detected distribution of multicharged ions. Thus no multiple acquisitions at different pH values will be necessary when this prediction is valid. Multi-channel data recording not only allows for obtaining single-channel data for each ion beam but also provides sufficiently large dynamic range and better description of the mobility peak profiles. These improvements may be used to increase the throughput from an ion source to downstream instruments/methods and they also provide additional information about the investigated samples complimentary to the mere summing of the data from different ion beams. Namely, processing intensity distributions of multi-charged ions as a function of the solution pH provides structural information of the biomolecule based on variations of $pK_a$ (or $pK_b$) values for the specific sites which are able to retain (or remove) protons or other charges species. Computer analysis of intensity distributions of deuterium-substituted ions provides additional information of this kind. Recording complimentary positive and negative ions formed during the decomposition of zwitterions would provide unambiguous sequence information for corresponding biomolecules which may be effectively expanded by collision or photo-induced dissociation of chosen ions. The resulting instruments and methods are useful for quantitative and/or qualitative, structural chemical and biological analysis.

In one aspect of the present invention, one introduces, under computer control, pH adjustors (such as, for example, acid/base buffers) and deuterated solvents directly into a capillary tube in which the sample solution (or solvent for DESI and aerosol particles measurements embodiments) is moving. The addition of pH adjustors may be regulated by a downstream feedback signal, such as the signal from a downstream pH measuring device. At the end of this capillary, essentially neutral droplets are formed by the assistance of a nebulizer gas flow. Their splitting (or that for droplets from the surface in case of DESI) into smaller charged droplets and further evaporation of these split droplets are provided by sound frequency resonant electric field and by microwave heating. Additional flow of hot gas would be introduced to prevent ion cluster formation after ions exit the microwave heating and splitting region. Such an approach is quite different from approaches whereby charged droplets are extracted by a strong electric field. Field penetration inside the solution (significantly increasing near the sharp edges of the capillary) is likely the main reason why charge distributions of recorded ions in a typical electrospray mass spectrum contain many highly charged ions which are substantially different from the charge distributions of the ions in the bulk solution. Extracting positive and negative ions and forming charged droplets in softer conditions coupled with their fast evaporation will likely result in ion charge distributions similar to that of the ions initially in solution. It is also possible to accumulate positive and negative ions from the initial flow in gas dynamic electric ion traps. This allows for the collection of ions almost continuously while a previous portion of ions is moving through the ion mobility cell and being recorded. It gives significantly higher sensitivity.

Orthogonal ion mobility injection also provides a narrower initial ion package entering the individual mobility cell channel (compared to single coaxial ion injection from an electric gating mechanism or from a co-axial trap) and this assures a significantly improved resolving power even as the continuously produced ions are being mobility and mass analyzed and recorded. A small gas counter flow coming from the mobility cell channels may optionally be used to prevent neutral species and very large singly charged ions from entering the mobility cell. Thus, wall contamination of ion optics and cluster ion formation during their motion through mobility cells will be significantly reduced. Also lower background signal and chemical noise will result. The most advanced version of the proposed system comprises four sets of mobility cells and four multi-beam TOFMS instruments (for the aerosol particles measurements embodiment this number may be even increased to 6). One IM/MS pair analyzes positive and negative ions formed in the initial ESI flow. The other pair (orthogonal to the first pair) measures ions formed from the neutral species of the initial ESI flow. In an IM/MS pair, the positive IM/MS and negative IM/MS goes orthogonally from the initial axis in two opposite directions. The four multichannel IM cell arrays generate four weak gas flows orthogonal and pointing to the axis of initial sample flow. Ions present in the initial ESI beam are going to traps under balancing forces from electric fields and gas flows. The four gas flows constrain the neutral species form the ESI beam close to the initial ESI beam axis. Among the neutral species, zwitterions may be of most interest as their formation will be governed by the controlled pH value of the sample solution. Zwitterions are formed from biomolecules whose isoelectric points close to the given pH value. Ions can be formed in this case by internal bond breaking of neutral zwitterions. Thus, a relatively low fluence laser beam could produce such ions and avoids formation of ions from other neutral species. Other types of chain breaking ionization techniques could also be used such as low energy electron attachment. After ion accumulation in traps, positive and negative ions are introduced against the buffer gas flow into the two multi-channel mobility cells. Once the largest desired ions reach an ion mobility (IM) channel entrance the electric field moving ions to these traps is switched to zero and the entrance fields allowing ions to penetrate the other IM channels (whose axes are orthogonal to the initial ESI beam and orthogonal to the plane of the previous pair of IM cells) are switched on and the laser beam for decomposing of zwitterions is pulsed. After introduction of produced ions into corresponding mobility cells, a new ion accumulation/trapping cycle starts. With suitable statistical treatments the negative and positive fragments from the intact neutral zwitterions may be detected in coincidence in each set of opposing mobility cells so that additional structural information is simultaneously achieved.

Another embodiment uses the pH-controlled electrospray to deposit solutions providing a specific isoelectric point separation of biomolecules on a surface from which the molecules may later be desorbed by an energetic source such as a laser, or particle beam before, during, and after the solution comes to dryness. This surface may be one comprising known MALDI matrices including nanoparticulates or it may be specially engineered to enhance desorption of neutrals which may then be fragmented to create oppositely charged ions if the desorbed neutral is zwitterionic. Electron attachment of hydrogen-insertion or other negative or positive ion attachment reactions are also possible ways to create a gas phase ion containing only one negative, or one positive charge overall.

In one possible application, elemental or alloy cluster ions or elemental or alloy cluster ions within a nebulized droplet are impinged upon a surface to generate ions from the molecules or atoms present at the surface. These secondary ions and neutrals are carried into the IM cell where they can be analyzed. In another application, pure solvent droplet aerosols or other aerosolized nanoparticulates are used to impinge the surface layer to desorb analyte atoms or molecules. In application, pneumo-sprayed droplets of solution (with or without acceleration of the droplets) are directed to the surface sample and after "reflection" from the surface enriched by the sample species are inserted into desolvation region. In still another application, an on demand droplet generator or a vibrating orifice generator may be used to form aerosolized droplets, which may contain analyte or analyte and nanoparticulate matrices, and these droplets are supplied at a rate which will place a train of equally spaced droplets into the gas stream so that each droplet can simultaneously be in front of two (or four) opposing IM channels at which time all particles can be simultaneously desorbed by energetic particle beams which may include a laser. This was described in co-pending U.S. application Ser. No. 11/025,640 filed Dec. 29, 2004 and published as U.S. Published Patent Application 2005/0230615 A1 and incorporated by reference as though fully described herein).

In an additional embodiment, a surface is located beneath the opposed multi-bore IM cells and multiple spots of the surface are alternately (or simultaneously) irradiated with multiple laser beams (see co-pending U.S. application Ser. No. 11/056,852, filed Feb. 11, 2005 of Russell et al, and published as U.S. Published Patent Application 2005/0242277 A1), incorporated by reference as though fully described herein) so that ions and post-ionized neutrals which are desorbed from individual regions on the surface are all registered in their own IM channel of the multi-bore IM array. Such a surface might be a biological tissue, or a synthetic surface, or a structured surface such as a microarray. Another application of this configuration could be the direct analysis of neutrals, ions, and zwitterions directly desorbed from an electrophoretically separated and heavy metal stained 2D gel. In yet another embodiment the surface or microarray may be located outside the opposed multi-bore IM structure and a gas stream can be used to entrain neutrals and ions for transporting through the region orthogonal to the axes of the multi-bore IM arrays which is between the IM multi-bore arrays.

The apparatus may also be applied to the analysis of atmospheric aerosols. These atmospheric aerosols can include whole cells either within solvent droplets or as isolated aerosolized cells. Other nanoparticulates or micron-sized particulates either within a droplet or as an isolated particulate can also be analyzed. The analysis can be assisted if the solvent droplets contain desirable matrices to assist in particle desorption from the aerosols. The apparatus could be used for analysis of isotopically-labeled drugs or other desired isotopically-labeled analytes.

In applications where ion mobility cells filled with a buffer gas are used as a volume/charge separation stage before analysis in a mass spectrometer, the cooled ions exit through a small aperture into a differentially pumped low pressure region before high vacuum part of the mass spectrometer. To minimize transmission ion losses at the exit orifice of the ion mobility cell, the ion beam inside the mobility cell should be focused. In the region between mobility cell and the high vacuum TOFMS, a narrow beam allows for the use of a very small aperture to limit the gas flow. The ion beam should also be cooled as much as possible and have a low divergence for optimum TOFMS operation conditions. If this divergence is small in both directions orthogonal to the direction of the main motion of ions, it is possible to introduce into the TOFMS, not one, but multiple ion beams which should be separated from the ion source to the detector to increase the instrument throughput proportionally to the number of ion beams. Such approach is feasible because: (i) multi-channel data recording (multi-channel time-to-digital (TDC)) devices are widely produced and used and (ii) it is possible to transport ions after mobility cell inside multi-channel RF-ion guide without noticeable losses and to focus ions into small entrance apertures in front of TOFMS thus having an applicable pressure inside it. The concept of multi-beam ion separation and measuring naturally incorporates the idea of orthogonal injection of ions coming from a continuous ion source, which proved to be so fruitful in TOF instrumentation, to the case of ion mobility spectrometry. However, here it is possible to enhance the efficient use of sample by manipulating gas flows and electric fields. Namely, it is possible to simultaneously insert and use positive and negative parent ions (wherein the ion source can simultaneously produce them) as well as the post-ionized neutral species of the initial sample flow. This is all the more beneficial for the analysis of zwitterion biopolymers whose presence is controlled by the pH of the solution and appear often as neutral molecules comprising equally numbers of spatially distributed positive and negative charge. Due to differences in isoelectric points only some of the biopolymers present in the sample could be neutral in the form of zwitterions at a given pH value. A relatively low energy (about 2 eV) is sufficient to cause bond breakage in the zwitterions and create ions (additional few eV may be necessary for separation of created ions of opposite sign), whereas direct ionization of organic molecules may demand the energy close to 10 eV. Thus high selectivity in producing ions from biomolecules of interest may be achieved. In addition, it is possible to trap ions before the entrances of multi-channel mobility cell by balancing forces from the electric field and the counter gas flow. Using different electric field strengths allows trapping of different type ions in different traps. Thus some additional ion pre-separation prior to the mobility channels may be achieved. This pre-separation will enhance the efficiency of the overall final ion separation.

New Source for Microwave Manipulation of Solvent Droplets in a Gas Flow

FIG. 1B schematically illustrates the method of getting ions from droplets, trapping of ions and neutrals, post-ionization of neutrals and orthogonal injection of ions into multi-channel ion mobility detection units (400) common for different embodiments of the present invention. An initial gas flow entraining quasi-neutral droplets (40) from a solution containing analytes is directed through the capillary which his surrounded by a solenoid (10). In one embodiment, a microwave voltage source may be coupled to the source. Microwave voltage (MV) (11) is inserted through a capacitor to the central coil of this solenoid. Due to capacitive coupling between the coils of the solenoid MV would be transferred to them producing the field inside the solenoid. To prevent irradiation of this field outside the solenoid a grounded shield (26) is located around it. The length of the solenoid is equal to the half wavelength of the microwave field. Thus, a standing wave would be formed inside the solenoid so that the maximum absolute value of field strength would be in the middle of the solenoid and zero field strength at its ends. The same solenoid is used for inserting (15) DC voltage (through a resistor (300) and sound or ultrasound frequency AC voltages (through a capacitor (500)) to the left most coil of the solenoid (10) (as shown in the figure). The last (right-most) coil of the solenoid is grounded (25). Thus, the gas flow heating, as well as the droplet oscillation and microwave heating are provided inside the solenoid. To achieve high efficiency the resistance of the solenoid and its inductance should be sufficiently large so that a realistic current for heating and an AC field strength for droplet splitting can be applied. The influence of resistance and inductance of the solenoid on the microwave voltage is small because the capacitive coupling between its coils is much stronger for high frequency field. For an approximate average radius r of droplets it is possible to choose the frequency of AC voltage to provide resonant splitting of the droplets inside the solenoid. Due to heating, the droplets evaporate and their sizes becomes smaller. When a droplet size approaches the optimal size for resonant frequency splitting, increasing the oscillations under high AC field results in splitting of the droplet into two droplets. Each of these two droplets may contain some excess of electric charge of opposite sign. Estimates show that opposite influence of droplet surface tension σ and viscosity η of the liquid results in two resonant radii of the droplet for a given AC frequency. The resonance frequency ω of the droplet oscillations for liquid of density ρ may be estimated using the following equation (obtained using approaches described in L. D. Landau and E. M. Lifschits, "Mechanics of continuum" Moscow, 1954):

$$\omega = \sqrt{\frac{8\sigma}{\rho r^3} - \frac{64\eta^2}{\rho^2 r^4}}.$$

Therefore for each droplet it is possible to have two chances for resonant splitting during its evaporation inside the solenoid under influence of a single harmonic AC voltage. As the energy of microwave droplet heating is proportional to the square of the field strength, small droplets in the region close to the middle of the solenoid may explode due to the high vapor pressure inside them. Therefore the formation of ions of both signs may be possible as these droplets are normally charged before the explosion. The resulting species are mixed with hot gas (typically, nitrogen) which prevents cluster formation and folding of zwitterions under influence of room temperature gas (preferably helium) flow (19) from mobility cells, and come inside the trapping region along the gas flow axis (23). The ions can be analyzed as previously discussed using the two opposed multi-channel IM units (400) shown.

Figure 2:
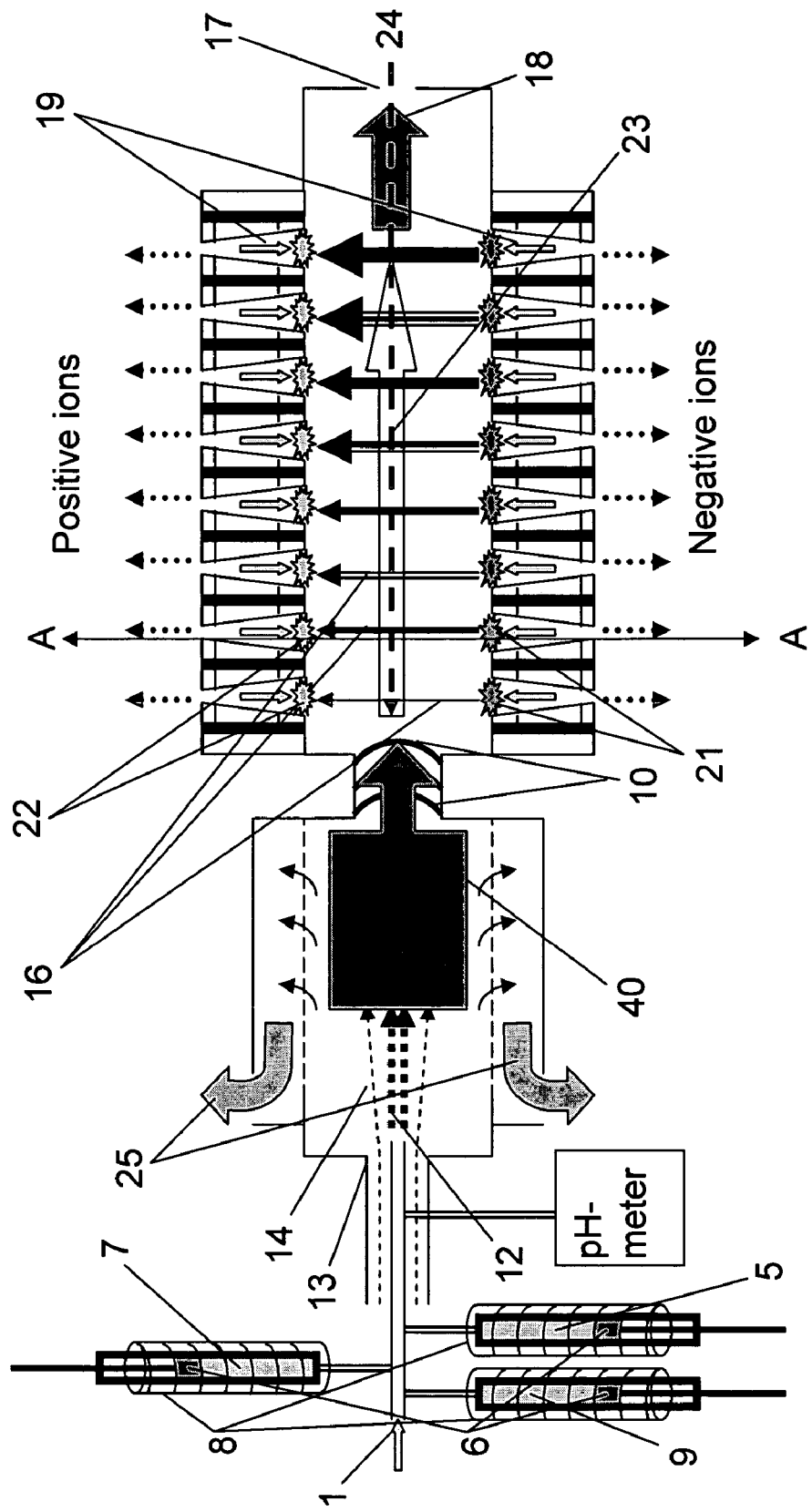
FIG. 2. Schematic view of the proposed electrospray interface.

A new approach for electrospray ionization of the sample solution is suggested to produce both negative and positive ions. It is schematically shown in FIG. 2. The sample solution (1) moves towards the end of the sample capillary tube located inside the nebulizer tube (13) and is mixed with the flows of acid or base buffers coming from syringes (7) and (9). Also, or alternatively, some flow of $D_2O$ (or another deuterated compound) may be added from syringe (5). These syringes have magnetic plungers (6) which can be moved by electromagnetic coils (8) controlled by computer. A higher current in the coil provides stronger pressure to the plunger, which increases the flow of the buffer liquid or deuterated substance directed to the sample capillary. Thus, the pH of the investigated solution and/or concentration of species containing deuterium can be varied. A pH measuring device is located downstream of the capillary. The measured pH value is read by computer, and can be used as part of a feedback loop. The nebulizer gas flow (14) forms a flow of fairly neutral droplets (12) from the sample solution. No DC electric field is applied in this region in contrast to conventional electrospray ion source where only positive or negative ions are extracted. The use of a high DC electric field, perhaps, is the main reason for the drastic difference in charge distribution of ions in solution and finally in the gas phase. (see Kelly, M. A., Vestling, M. M., Fenselau C. C., Smith P. B.; "Electrospray Analysis of Proteins—a Comparison of Positive-Ion and Negative-Ion Mass Spectra at High and Low pH" *Org. Mass Spectrom.* 1992, 27, 1143-1147). The nebulizer gas may be heated up to a temperature slightly below the boiling point of the solution so that ions in solution can rapidly reach the charge equilibrium state. Just after the tip of the sample capillary, a sound frequency voltage close to resonance is applied for droplet splitting (15). According to the calculations for water droplets of about 0.1 mm diameter, this frequency should be about 4.5 kHz with an amplitude of a few hundred volts. Such conditions should be adequate to rapidly (about 1 msec) split these droplets into smaller ones having some excess positive or negative charge. The accepted mechanism of droplet evaporation and further splitting proposed in conventional ESI sources through electrostatic explosion may be also valid after such initial droplet splitting. The plates where the sound frequency voltage is applied, also prevent penetration of microwave voltage inside the sample capillary and overheating the liquid. The capillary could be made of glass and not have sharp conducting edges that would produce strong electric fields inside the capillary. Further evaporation of the solvent from these droplets is stimulated by heating of these droplets by microwave influence (11) and hot gas flow (10). Hot gas is introduced from two opposite directions orthogonal to the flow of droplets. A microwave electric field is applied in these directions too. Heating the droplets with a microwave has significant advantages in comparison to conventional single hot gas flow heating. Deposition of the energy from a hot gas to droplets is proportional to the droplet surface area to volume ratio so it becomes less effective for evaporation of large droplets. In contrast, the microwave energy deposited to the droplet for small droplets is proportional to the volume of the droplet. So it has the same or close efficiency for evaporation of each droplet. The microwave energy flow is easily controlled, has low power requirements, and does not transfer the heat to other components of the system, where it may be undesirable. Nevertheless hot gas flow (10), dry nitrogen, for example, would also be useful to prevent undesirable cooling of ions, possible cluster formation and folding of zwitterions after they exit the microwave heating region. Some modulation of microwave voltage by sound or ultra-sound frequency voltages would be useful to split evaporated droplets (when their size reaches resonance). This will accelerate the process of droplets evaporation. It is reasonable also to apply some DC voltage to the plates (11) to separate positive and negative droplets and ions and to prevent their recombination. The direction of this field should be the same as further in the trapping region and the strength being enough to move only light ions formed from the solvent to the plates (11) only light ions formed from the solvent. Thus the flow of ion and neutral species (40) would be formed and directed to the trapping region (it may be referred also as orthogonal IM injection region).

Although the examples provided for introduction of pH modifiers and dueterated compositions to the sample have been limited to syringes, it should be understood that the means for introduction of these compositions are not so limited and include any and all such techniques and manual and automated apparatuses (including all flow injection techniques and apparatuses) known to those of ordinary skill in the art as well as any such methods yet to be developed.

If the charge distribution of the ions formed in the ESI interface is close to the initial charge distribution in solution, it will not be necessary in each case to collect data for a large number of different pH values. For example if the problem is to determine the presence and possibly the concentration of a known (small) set of biopolymers whose isoelectric points have been previously measured, it is possible to simply collect data at these isoelectric points, i.e., at the corresponding pH values using adjustable syringe pumps (7) and (9). These pumps should be calibrated beforehand. For each isoelectric point, zwitterions should be concentrated along the axis of the orthogonal IM injection region and "cleaned" from positive and negative ions as described before. After decomposition of the zwitterions, the complimentary positive and negative ions (whose sum of masses gives the mass of the biopolymer under study) should be searched. To reliably identify a positive-negative daughter pair, their intensity distribution over the ion beams should be proportional to each other within the experimental errors (the difference in the absolute intensities may be due to different ion transmissions). These ion intensity distributions depend on gas flow force applied to the zwitterion and its diffusion coefficient. Further, it would be useful to compare ions generated from the same pulse. It is possible to change the amount of the given zwitterions in solution and in the sample flow by changing slightly the pH of the solution. The intensities of the true complimentary ion pair should change proportionally. Tuning the energy of photons in the laser beam should result in a similar change.

The characterization of unknown biopolymers in solution may also be simplified if the ion charge distribution in solution is measured as previously demonstrated in the art (see, M. O. Raznikova, V. V. Raznikov: "Determination of the extent of activity of H-atoms in ions of polyfunctional compounds by H/D exchange mass spectra" *Chimicheskaya fizika*, v. 24, N1, c. 3, 2005 (in Russian)). This method allows one to determine the probabilities of charge retention (positive and negative) on each site in the biopolymer using the intensity distribution of the multi-charged ions of the particular biopolymer. For a given pH value of the solution, the corresponding $pK_a$ values for a given biopolymer could be calculated using the probabilities of charge retention so that its isoelectric point (pI) could be predicted (sum of pKas divided by two). Besides the distribution itself, the maximum numbers of positively and negatively charged sites in the given biopolymer molecule should be determined. This information can be obtained by doing measurements at extremely low and at extremely high pH values followed by determination of ion peak with maximum charge for given polymer. The first measurement will give the maximum number of positive charges of ions from the given biopolymer, i.e., the maximum number of positively charged sites ("negative" sites will be neutralized). The second measurement would give the maximum number of negatively charged sites.

The biopolymer conformation, and thus its pKa values, are likely to change over a wide pH range. In this case, the previous method would not be reliable for such "long distance" prediction of pI values. It may then be better to use multi-charged ion distributions with shorter predicted distance to isoelectric point or gradually approach the true isoelectric point by changing the pH around the predicted starting point and find the pH giving maximum intensity to confirm the isoelectric point. At the isoelectric point, collision-induced dissociation of some or all found complimentary ions separated in multi-channel IM cell may give unique structure information which would be more reliable than that provided by existing methods using a comparable analysis time and with comparable amount of the sample. Our three (or four)-dimensional separation method (isoelectric point, ion mobility and TOF mass analysis (or TOFMS/MS) gives extremely large space for characterization of the components in the sample. With this approach, the use of sample is optimized. The isoelectric point separation can be performed in a controllable, dedicated way. If the $pK_a$ values are calculated for all possible charged sites in the biopolymer, the possibility of erroneous interpretation of the data will be reduced. It would indicate the types of residues which carry charge in the biopolymer and, perhaps, provide information about their environment. Additionally, mobility measurements can provide information about the conformation of the molecule. Fairly good mobility resolution of multi-charged ions and their selective collision induced dissociation can be important to solve some structural problems also. In necessary cases, additional information or even supplementary ion separation may be provided by controllable addition of deuterated solvent into the sample flow by the syringe (5). The intensity distributions for peaks with different number of H-atoms substituted for D are different not only for different molecules but for different conformations of the same molecule. Using an approach similar to that mentioned above for the method of analysis of distribution of multi-charged ions (see M. O. Raznikova; V. V. Raznikov; "Estimation of Probabilities of Protonation of Amino Acid Residues in Peptides and Proteins by their Electrospray Mass Spectra" Chimicheskaya fizika, vol. 20, N. 4, c 13, 2001) it is possible also to interpret the measured intensity distribution of deuterated ions in order to estimate the probability of H-D substitution for separate sites in the molecule. This gives an opportunity to determine the numbers of different functional groups having labile H-atoms ($—NH_2$, >NH, —OH and so on) and, perhaps, draw some conclusions about their structural orientation in solution (see M. O. Raznikova, V. V. Raznikov, "Determination of the Extent of Activity of H-atoms in Ions of Polyfunctional Compounds by H/D Exchange Mass Spectra" Chimicheskaya fizika, vol. 24, N. 1, c. 3, 2005). The distributions of ions may be also modified if an additional syringe is used to add a specific fast acting enzyme to the solutions which would cause cleavage of biomolecules (and subsequent ion formation of these fragments according to equilibrium conditions in solution) prior to the droplet formation as the solution exits the capillary.

Figure 3:
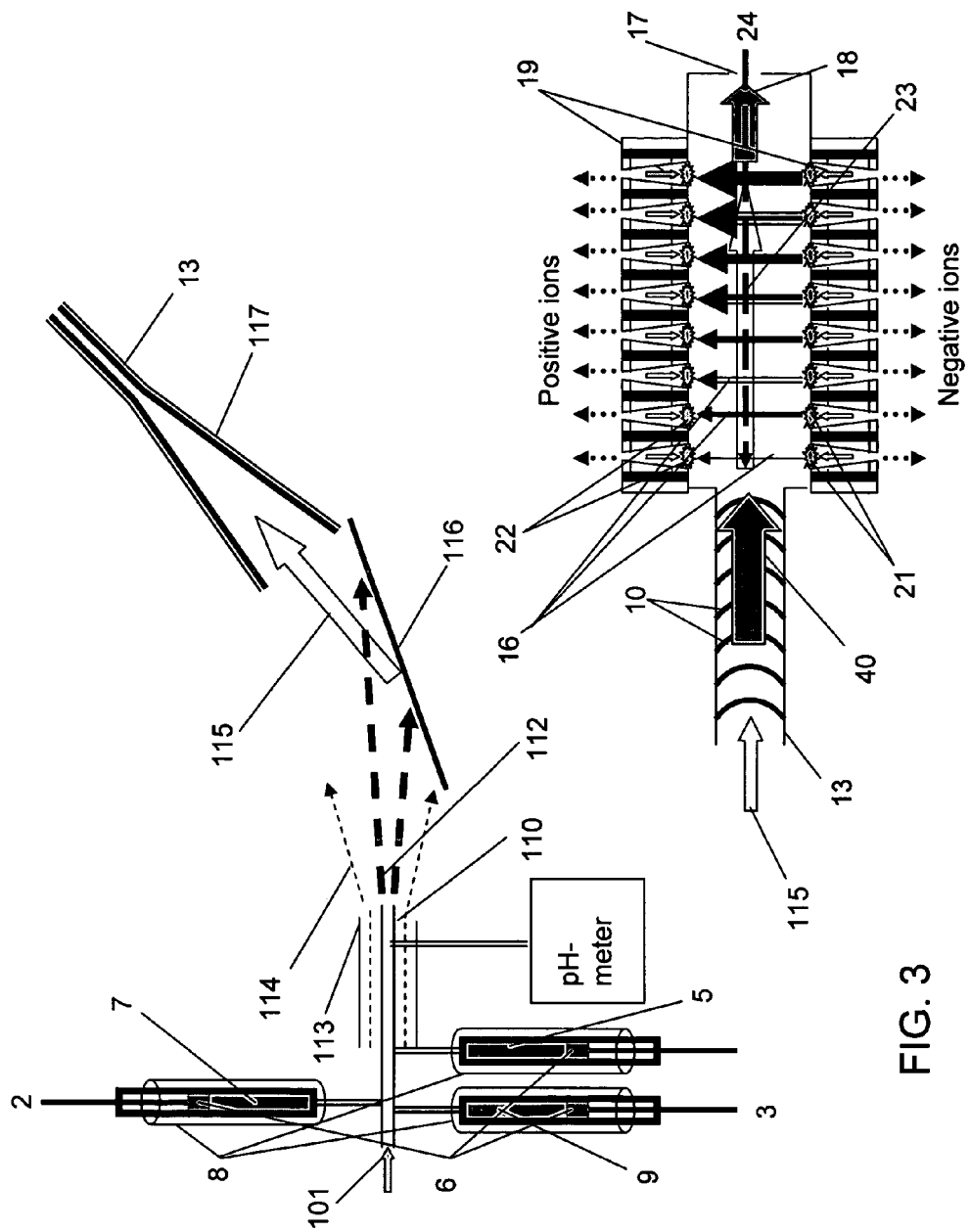
FIG. 3. Schematic view of the proposed electrospray interface with bombardment of the sample surface by solvent droplets (for DESI version).

The previously described approach will work not only for direct analysis of solution but also for bombardment of the sample surface by cluster ions, or solvent droplets containing nanoparticulates (see pending U.S. application Ser. No. 10/861,970, filed Jun. 4, 2004; pending U.S. application Ser. No. 11/231,448, filed Sep. 21, 2005; and U.S. Pat. No. 6,989, 528) or in DESI mode of operation using a droplet source (110) which is a modification of the electrospray interface as is shown in FIG. 3. Many parts of this interface are the same as those shown in FIG. 1 and FIG. 2, the exception being the nebulizer capillary (113) is open to the ambient air and the fact that a pure solvent stream (101) is employed. The injector tube (13) to the desolvation region is marked as in FIG. 2 and the remainder of the assembly is identical to FIG. 2. Instead of investigating a solution containing the analyte (as in FIG. 2) we are using a flow of solvent (101) which is inserted into the capillary. Droplets of pH adjusted solvent (112), emerging into the nebulizer gas (114) are directed to the moveable surface sample (116) under atmospheric pressure. These droplets may be neutral or they may be charged by appropriate biasing of the capillary and appropriate electrodes to accelerate the droplets toward the surface. "Reflected" droplets (115) enriched by species taken from the surface sample (116) by the gas flow are inserted into conic part of injector (117) which is connected with a cylindrically symmetric funnel entrance of the injector (13) capillary. This injector (13) maybe heated to prevent droplet condensation and adsorption of the sample species on the walls. The inside pressure can vary over a wide range from a few mTorr up to near atmosphere which is adjusted by the sizes of capillary (13) and (17) and the speed of the pumps (24). The length of this injector should not be very short and would be chosen experimentally to provide enough time for species from the sample to come to charge state equilibrium (and, perhaps, for H-D exchange too) with the solution inside the droplets. Heating and splitting of droplets is provided as before by a microwave voltage modulated by several sonic or ultrasonic frequency voltages applied to the solenoid (10) shown in more details in FIG. 1B. Further transformation of the flow and methods of measurements are the same as described in the previous sections both with RF trapping operations at low pressure and without RF trapping at higher pressures near or above atmosphere. The configuration in FIG. 3 is very versatile for surface analysis. For example, an energetic ion source (such as a laser or a particle beam) could be combined to irradiate the surface (116) during droplet impingement. This would function to erode the surface either prior to, during or after droplet impingement. The energetic source could also be used to pre-form ions on the surface either by direct ionization or by matrix assisted laser desorption. In another configuration, an on demand droplet generator in place of the (110) could be used to impinge either neutral or charged droplets. Laser light scattering velocity tracking of the droplets could accurately predict when and in what spatial region the droplet was going to impinge surface (116). At the moment just as the droplet was impinging the surface a laser could also be pulsed to irradiate the droplet and surface. The droplet meniscus would act as a lens to micro-focus the portion of the laser beam which had impinged the droplet into a high fluence spot immediately below where the droplet was hitting the surface (116). In this way a MALDI plume would be produced from an area less than the size of the droplet diameter. The ions and neutrals from the plume would evaporate from the surface into the oncoming droplet and then be captured and borne into the injector (117) entrance to the mobility cell array. The source may also be used with the teachings of Schultz et. al. (see U.S. Pat. No. 6,989,528; pending application Ser. No. 11/231,448 filed Sep. 21, 2005; and pending application Ser. No. 10/861,970, filed Jun. 4, 2004 and incorporated by reference as though fully described herein) to impinge droplets which are either pure solvent or which contain nanoparticulates which can act as MALDI active matrices and as taught in these applications the droplet can function both to sputter the surface into the injector (117) while depositing the matrix active material. Energetic particle irradiation of the surface can be synchronized before, during, and after the droplet arrival at the surface (116).

In the context of the present invention, four measuring units (400) each including a multi-channel IM cell combined with a multi-channel data recording TOFMS (FIG. 4 which is a view along the cross-section A-A of FIG. 1B) are used to collect and detect positive and negative ions (i) directly produced from different ion sources and co-mixed with a gas flow. (40) including ESI ions (or laser ablated ions, or chemical ionization of neutrals or post-ionization of neutrals or neutral molecule with adducts) and (ii) produced from fragments of zwitterions. Ions of a given type are accumulated in the orthogonal IM injection region (41) in separate traps (42) for each ion beam as described in detail above and in FIG. 1A, FIG. 1B and FIG. 4. In FIG. 1B ions are pre-selected by a combination of electric fields and gas flows in the trapping region and are directed to different traps. For optimum conditions of ion trapping and further transport in mobility cells the gas pressure inside orthogonal IM injection region is maintained at about 100 Torr by pumping (49). After accumulation, ions move under increasing electric field into the funnel-shape IM channels (53), ions in the conical sections of the channels undergo a small gas counterflow. The remaining transport through each multichannel IM unit (400) has already been described.

Figure 6:
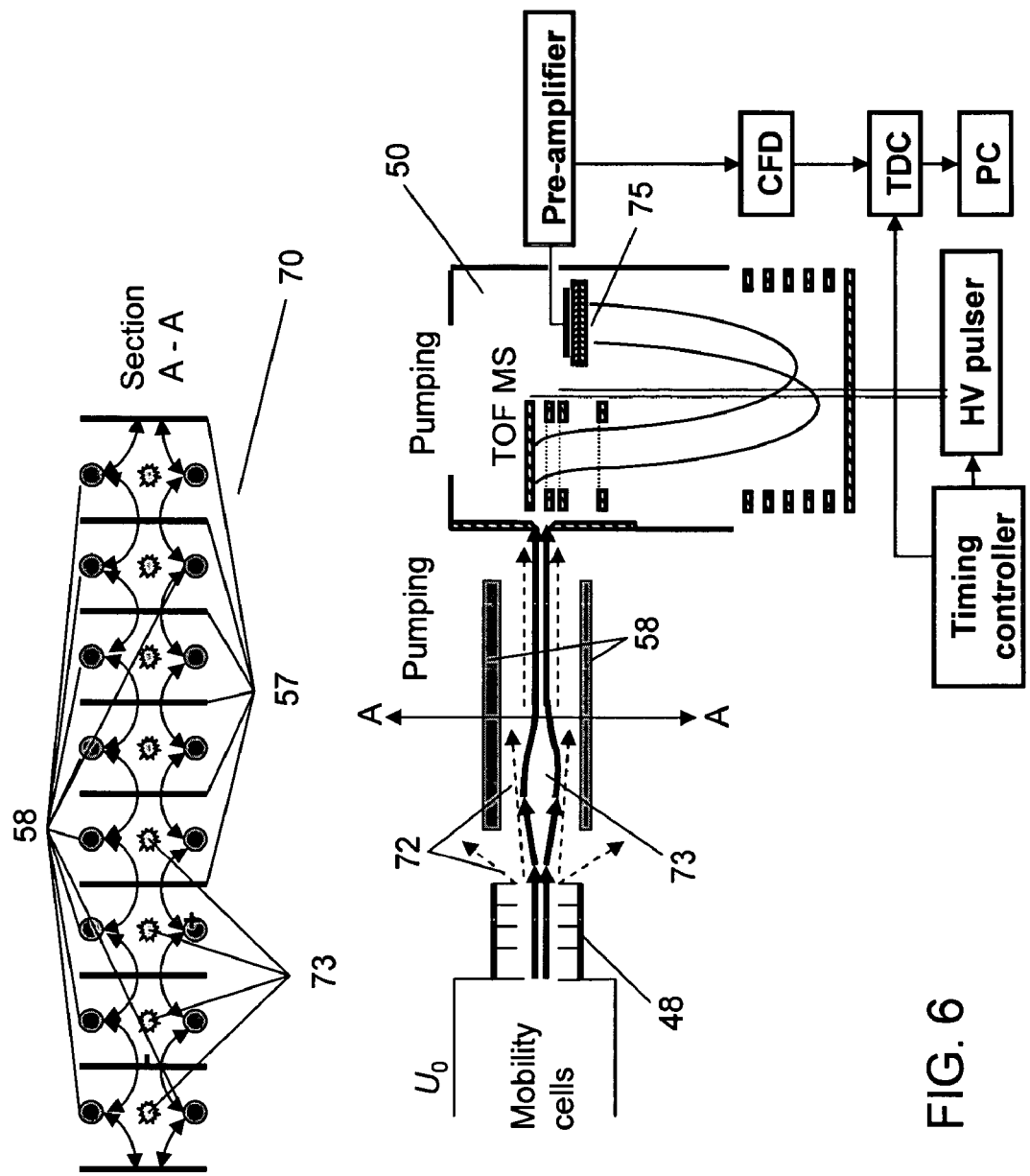
FIG. 6. More detailed schematic view (including cross-section orthogonal to IM ion beam) from the orthogonal direction of the RF-guide IM/TOF interface.

FIG. 6 gives details of the multichannel RF interface (70) to prevent ions from diverging from the axis by the gas flow (72). The main function of the CID tubes (48) is to collect ions coming from corresponding IM channels and transport them to the multi-channel RF interface (70). However, high electric field inside CID (48) tubes may be applied to provide collision induced dissociation of some chosen ions. To focus each ion beam (73), a multi-channel RF-ion guide (58) is used. This interface (70) shown in detail (section A-A) in the top part of FIG. 6 is comprised of pairs of rods (58) and confining plates (57) between each pair. RF-voltage of the same phase is applied to rods. DC voltages of rods and confining plates are the same. The voltage difference between the confining plates and the TOFMS (50) corresponds to the energy that ions need to enter the TOFMS and to be detected (determined by TOFMS geometry). These plates allow ion confinement (73) between rods. Ions (73) entering the orthogonal TOFMS (50) have some divergence and different velocities. Due to RF-focusing they are entering the TOFMS through small orifices below 1 mm diameter, thus a single pump (52) is sufficient for good operating pressure. Before entering the RF ion guide, ions have traveled through the IM cell and thus low m/z ions arrive first. The arrival time is roughly linear to m/z values. The slope of the mobility time versus m/z varies with the type of ions. As the focusing force provided by RF-field is proportional to quadratic voltage/frequency ratio and inversely proportional to the ion mass to charge ratio, it is possible to increase the amplitude of RF-voltage (or decrease the frequency) applied to rods proportionally to the square root of ion arrival time with the coefficient being the square root of the slope of the mobility time versus m/z. Such RF-field adjustment allows one to record small ions without defocusing and losing them due to possible instability of their motion for large RF-fields. Also, it provides an opportunity to effectively focus large mass ions and achieve similar width ion beams for ions of all masses. It is true for the singly charged ions and multi-charged ions will be focused better proportionally to their charge. Usually CID provides structural information about ions. Most valuable information about parent ions is usually obtained from daughter ions whose mass is close to the parent ion mass. It is possible to increase the RF-field proportional to the square root of the ion mass to charge ratio which is emerging from the mobility cell and thus have optimal transport of all ions through the RF interface.

Figure 5:
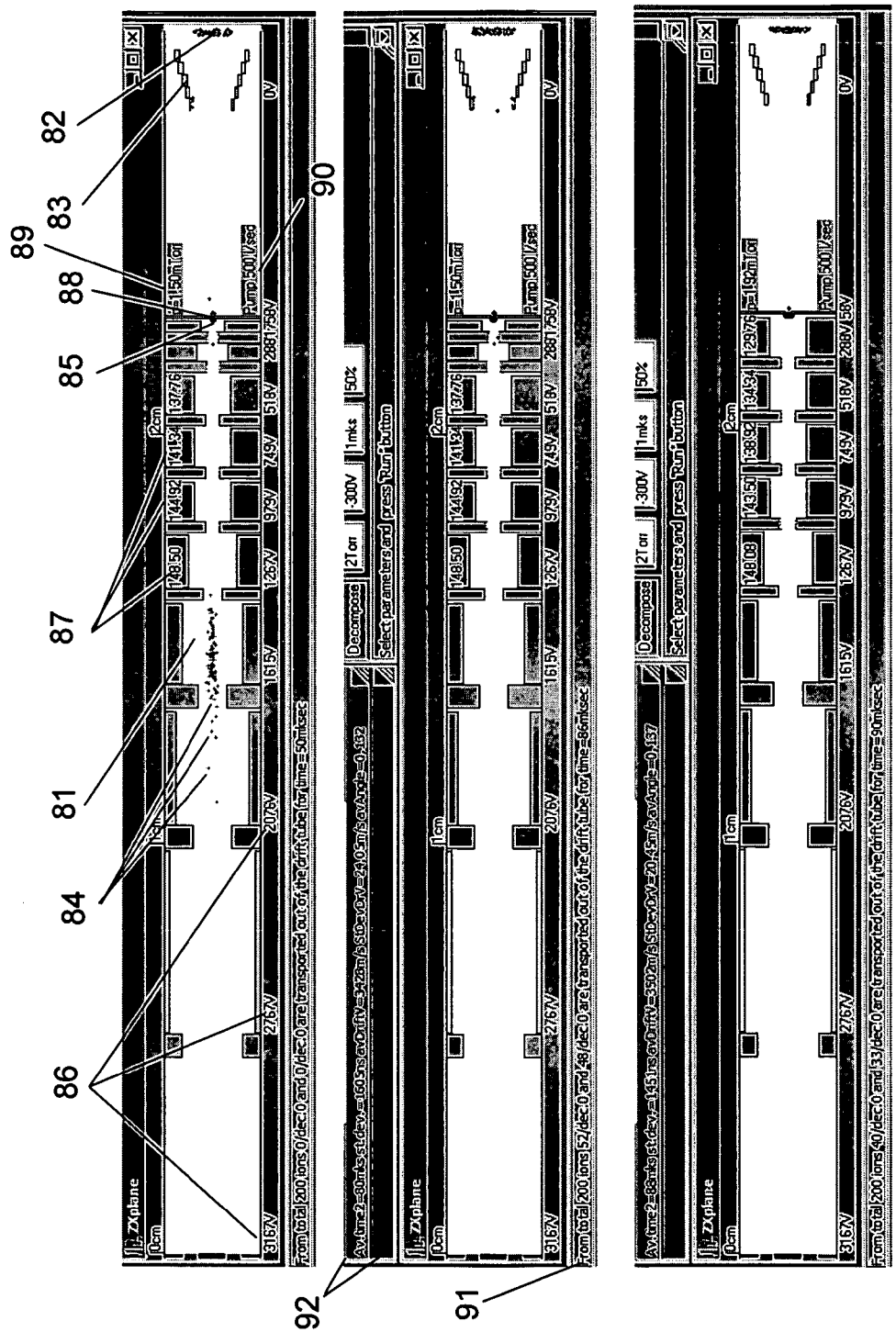
FIG. 5. Simulation results for short mobility cell with different focusing of ions at the exit of mobility cell.

FIG. 5 shows some results of computer simulation of ion motion in short (about 2 cm) mobility cells under 150 Torr helium pressure in the third chamber of the mobility cell (81). Two types of singly charged ions are shown: "light" ions, 720 Da mass, 100 $Å^2$ collision cross section, and "heavy" ions 1000 Da mass, 150 $Å^2$ collision cross section. The top window of the figure shows the moment when light ions (small dark grey (red) crosses (82)) are stopped inside the TOFMS (83) (shown as a cone at the right side). Heavy ions (small light grey (green) crosses (84)) are moving in the middle of mobility cell. The black small crosses (85) show discharged ions after their collisions to the walls. The voltages applied to electrodes are shown below (86). Gas pressures in Torr are shown for various chambers (87) on the top of the chambers (beginning of the forth chamber of mobility cell). The diameter of orifices between these chambers and the length of them is 1 mm. The diameter of the exit orifice (88) is 0.2 mm. Just after exit orifice on the top of the window residual pressure in mTorr is shown (89). Pumping rate (500 L/sec) is shown below (90). The final picture for the simulation is shown in the middle of FIG. 5. The status bar at the bottom (91) of this picture gives information about the numbers of ions of both types which have reached the final position of their motion. Here about 50% of them survived during this motion. Two status bars (92) at the left top part of the picture give the drift time in μs for each type of ions, standard deviation of mobility peak in ns, average final velocity of the ions, its standard deviation and average angle of ion divergence in radian. At the bottom of the figure the same final situation is shown for the case without special focusing electrode for ions near exit of mobility cell. The transmission of ions in this case is less (40% and 33%) but the resolving power (more than 25) is better than for the previous case (about 20).

Figure 7:
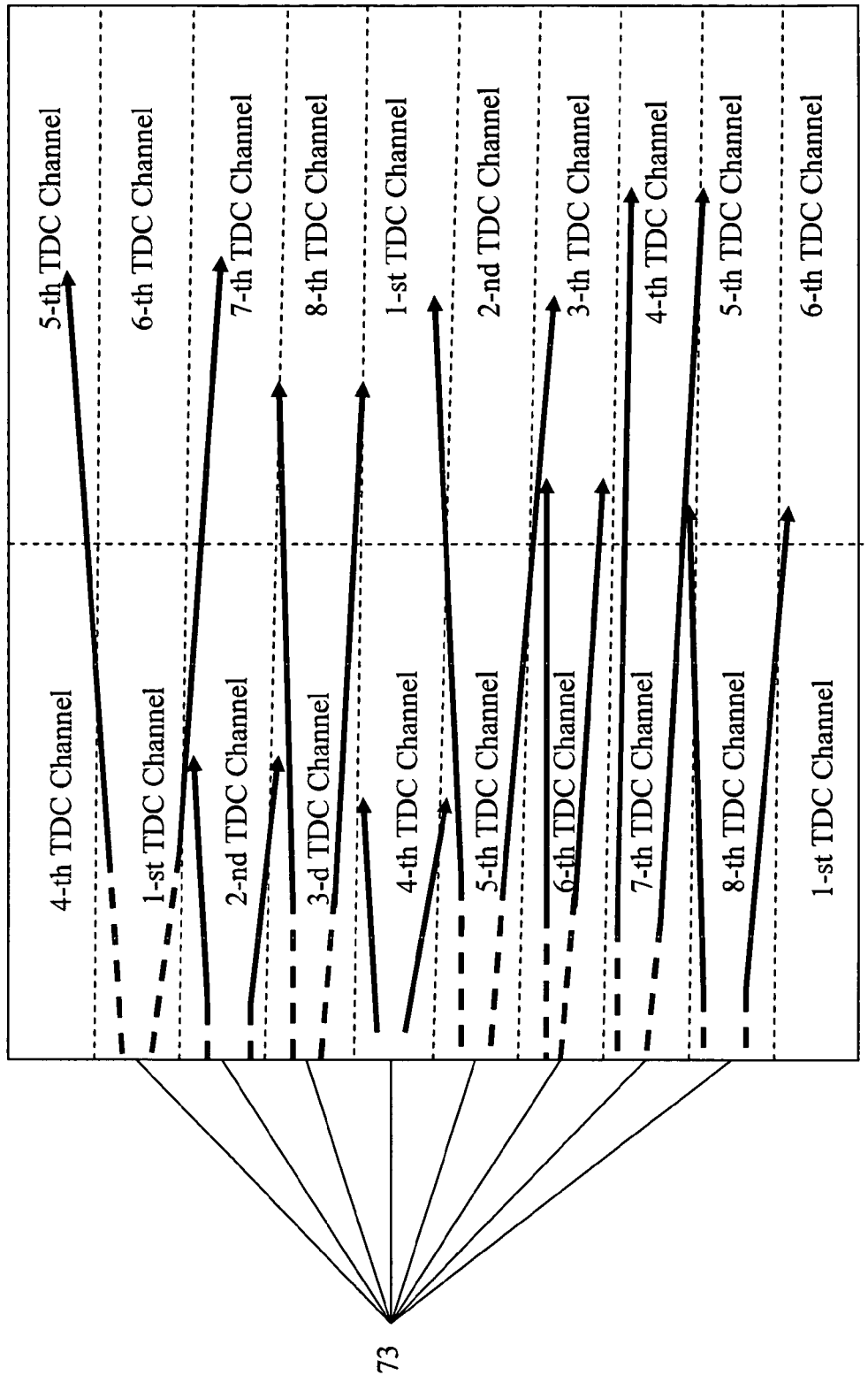
FIG. 7. Schematic view showing recording of separate ion beams in the TOFMS.
Figure 8:
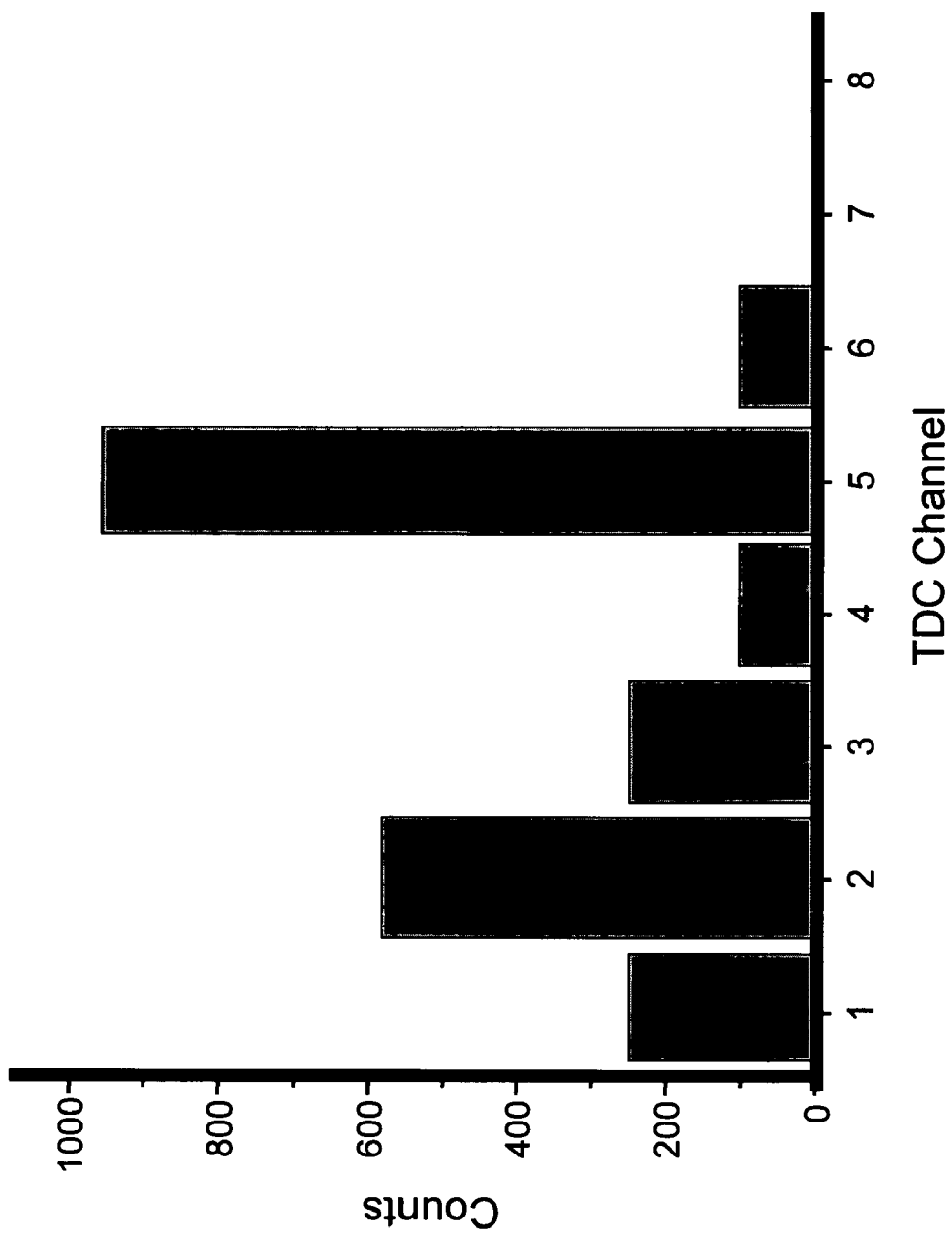
FIG. 8 Possible distribution of counts on the TDC channels contributed by the fifth ion beam.

Ion beams entering the TOFMS will have a width of about 1 mm and a divergence of about 0.02-0.04 radian (when special interface electrode assembly like (70) is used). If the maximum length of ion path in the initial direction to the detector plate (75) is about 10 cm, the standard deviation of the ion beam width in the plane of recording will be about 3 mm. As the distance between ion beams is about 5 mm, individual beams will overlap to some extent on the detector plate. So if the detector plate has eight anodes and each one is for recording the corresponding ion beam, it will actually record its own beam and some signals from the adjacent beams as well. This property seems to be a drawback but it may be turned into an important advantage. The fact that a small fraction of a given ion beam is recorded in an adjacent channel can be used to increase the dynamic range if the signal in the main channel is saturated. It is the same principle as that taught in U.S. Pat. No. 6,747,271 of Gonin et al., through the use of large and small anodes. It is particularly useful if there is no interference from the other signals on that adjacent channel. This can easily be achieved with the mobility and mass resolutions of the present instrumentation, and with multi-channel data recording. Since the IM channels are not likely to be identical, the same ions (same mass and formed from the same pulse) traveling through different channels will appear at different times so their signals will not overlap. The coefficients used to recover the signal in the main channel may be obtained by comparing the signals on the tails of mobility peaks, i.e. where the main signal is not (yet) saturated. These coefficients for known location and sizes of recording anodes could be easily converted into angle divergence of ion beams if the velocities of ions in axial direction are known. At the end of RF-ion guide, the velocity of ions will not be very high, but close to that in IM channels (few hundred meters per second for ion of about 1000 Da mass which corresponds to a kinetic energy of 0.1 eV). Accelerating voltage of several tens of eV applied between RF-ion guide and the TOFMS gives these ions a velocity of several thousand meters per second with relative standard deviation due to initial energy far less than 1%. Known angle divergence of ion beams allows estimation of the ion fraction impinging adjacent anodes. Thus, when an ion flow saturates signal in the main anode it may be recovered by the small unsaturated signal fraction impinging adjacent anodes. Also, better mobility peak profiling may be provided by multi-TDC channel detection. Several anodes are linked to the same TDC channel. An example of anode arrangement with their TDC channel links is shown in FIG. 7. In this case the distribution of ion counts for each ion beam (73) over the TDC channels (shown in FIG. 8 for fifth ion beam) will be used for calculation of ion intensities coming to the left and the right halves of the detector plate with correction of possible signal saturation using also the mathematical procedure of TDC dead-time correction.

Figure 9:
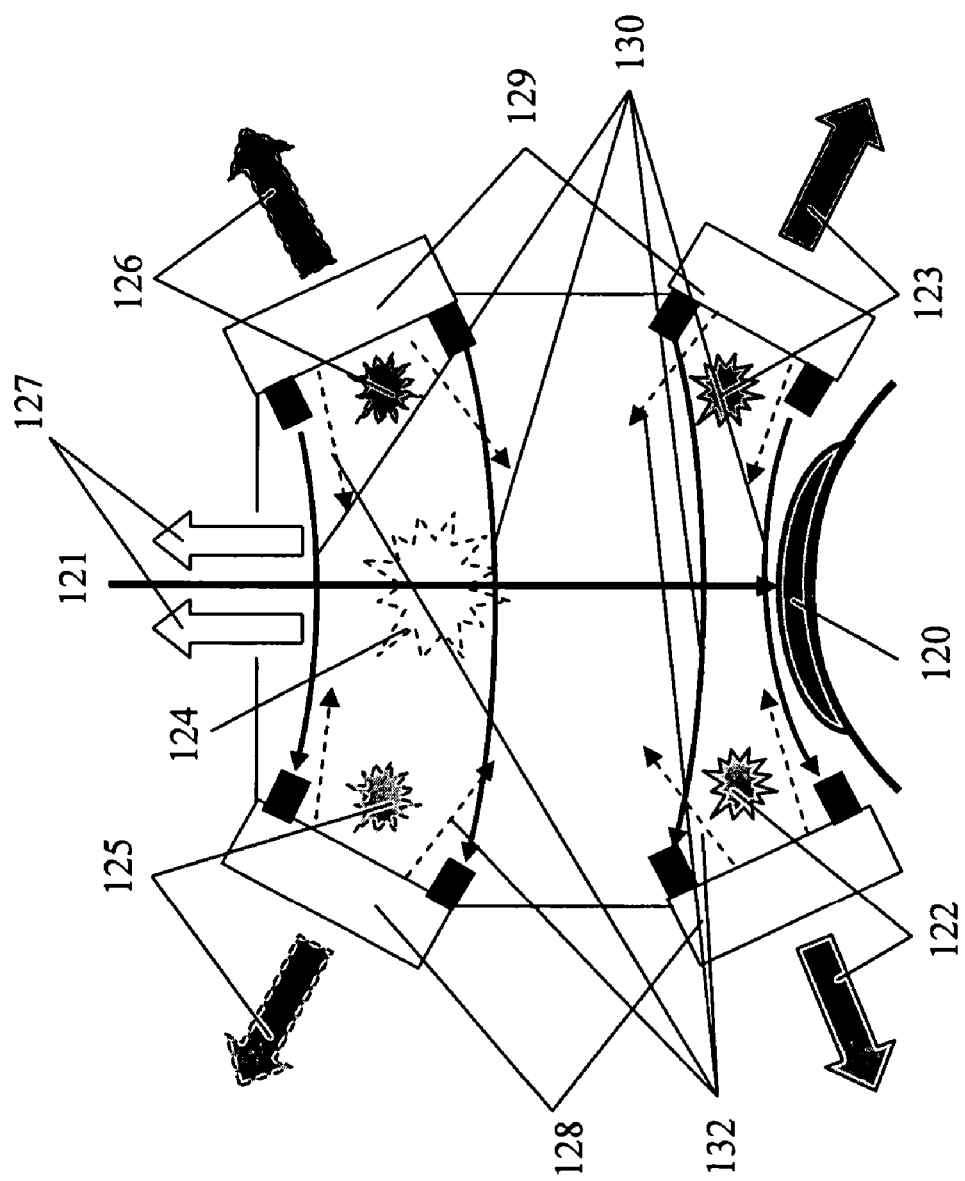
FIG. 9. Schematic cross-section of trapping region for multi-beam profiling of a sample surface.
Figure 10:
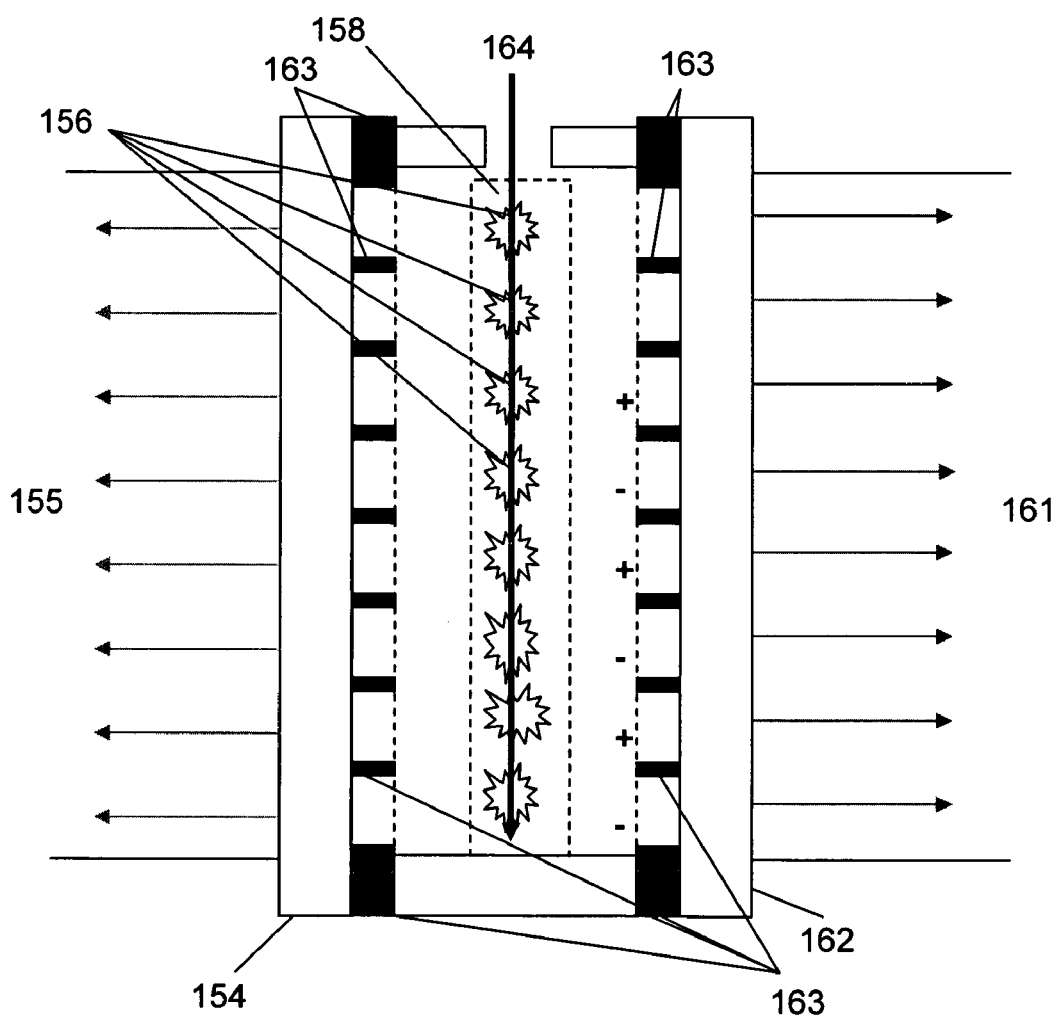
FIG. 10. Schematic view from the top of trapping region for multi-beam profiling of a sample surface.

FIG. 9 schematically shows the cross-section of the trapping region for multi-beam profiling of a surface sample (120) located on a convex cylindrical substrate. The view from the top of this region is given in FIG. 10. Several (eight for the figures) energetic pulsed beams (121) (for example laser or ion beams) produce evaporated sample plumes near the surface. Gas flows (132) from mobility cells (128) and (129) or the one created by pumping (127) provide motion of the plumes from the surface to the top of the figure. Any and all means known in the art to create, modify and control gas flows in this and all other regions of the apparatus may be used. Examples of means to create, modify and control gas flows include, but are not limited to, mechanical variable diameter iris type orifices, variable leak valves, or more sophisticated gas flow controllers, all of which may be under computer control. All other means known to those of ordinary skill in the art are also applicable, as well as any yet to be developed. The main factor here is the rate of pumping (127) which is provided through the slit (158). The others are the gas pressures at the ends of mobility cells (128) and (129). Electric fields (130) between bottom pair of mobility cells move ions from the plume; positive (122) to the left mobility cell and negative (123) to the right mobility cell. After some delay time after initiation of the desorption pulse, the neutral part of the plume (124), shown in FIG. 10 as (156), will have moved to the region between the two top mobility cells (128) and (129). At that time, a post-ionization laser pulse (164), shown in FIG. 11, can be used to produce positive and negative ions from these neutrals. Using an electric field (130) between the top pair of mobility cells (128) and (129) shown in FIG. 11 as (154) and (162) with collimating electrodes (163), one can insert positive ions (125) into the left cell and negative ions (126) are inserted into the right one. Thus, the flows of positive ions (155) and negative ions (161) inside the corresponding mobility cells are formed. The preferred means for post-ionization of neutrals is laser irradiation of the flow or plume containing the neutrals, however other means, such as, but not limited to, electron attachment, chemical ionization, use of a metastable atom beam, helium ion Auger neutralization, and other means known to those of skill in the art are applicable.

This embodiment removes one of the main restrictions to analysis by IM-oTOFMS of a sample surface. The drift time in the mobility cell is often longer than the time between applications of the energetic ion desorption pulse. If only one analysis channel is used then the rate at which the desorption pulses are applied is limited to the time necessary for the IM cell to clear on analyte ions. Thus if multiple beams are used, we approach or exceed the analysis time possible when one laser and an MS are used to interrogate a surface. An additional advantage is that the sample does not need to be translated as rapidly from one spot to the other if multiple channels are used in lieu of a single channel. This considerably reduces the complexity and improves the positional accuracy of the mechanical means of translating the sample to different spots in front of the immobile focal point of the desorption source.

Analysis of Aerosol Particles

Figure 11:
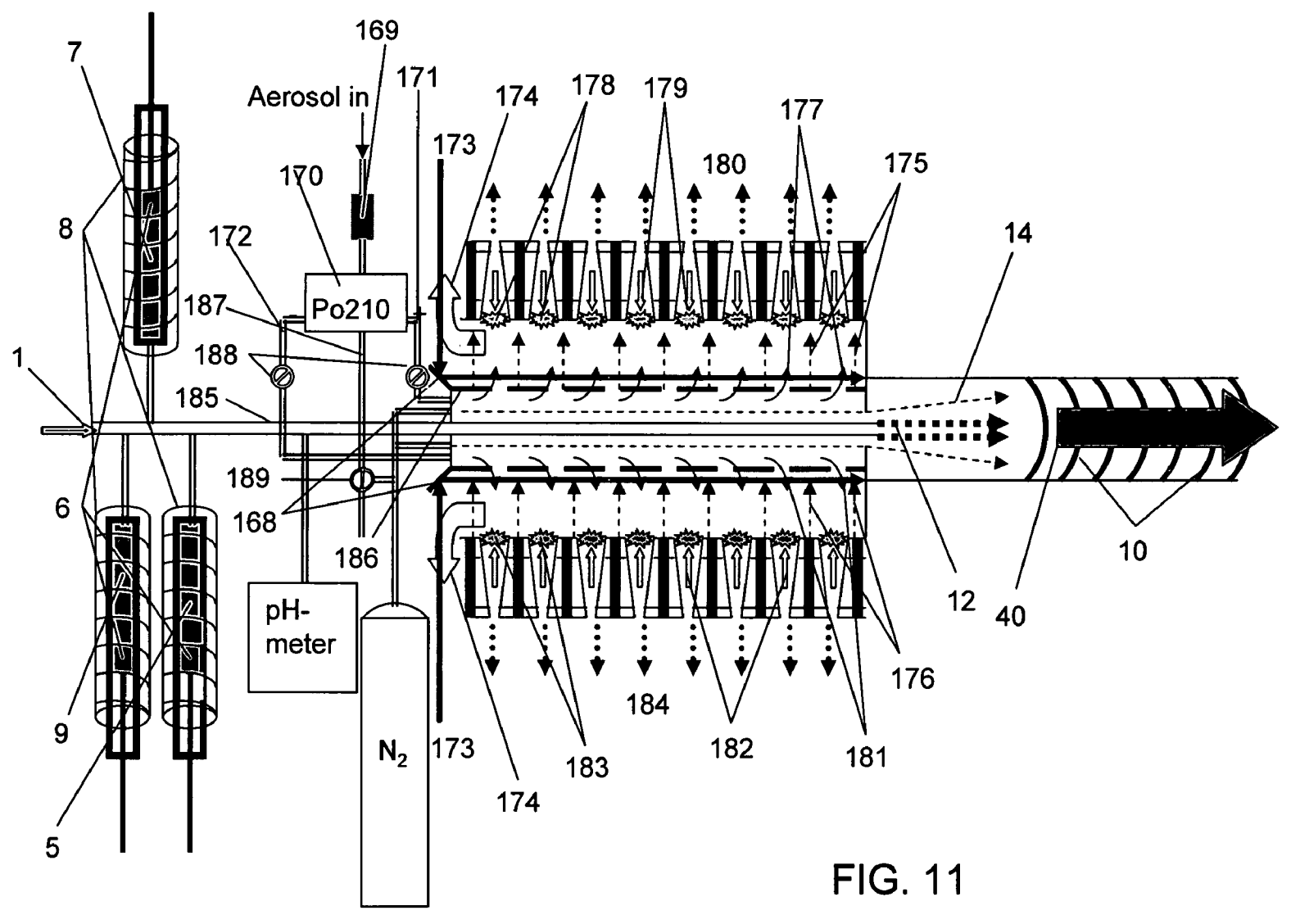
Figure 12:
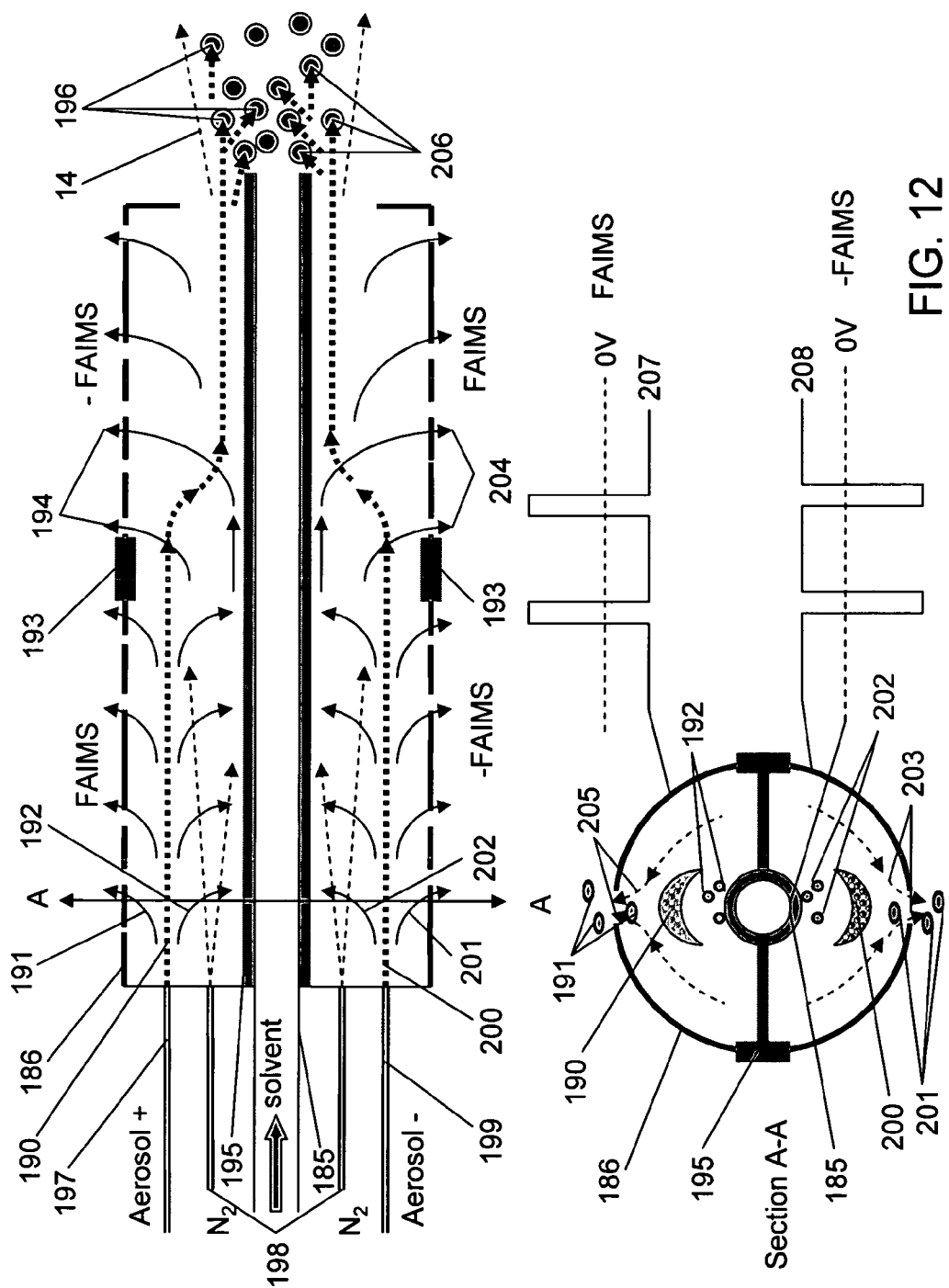
FIG. 12. Illustration of separation of charged aerosol particles before IM-TOFMS measurements.
Figure 13:
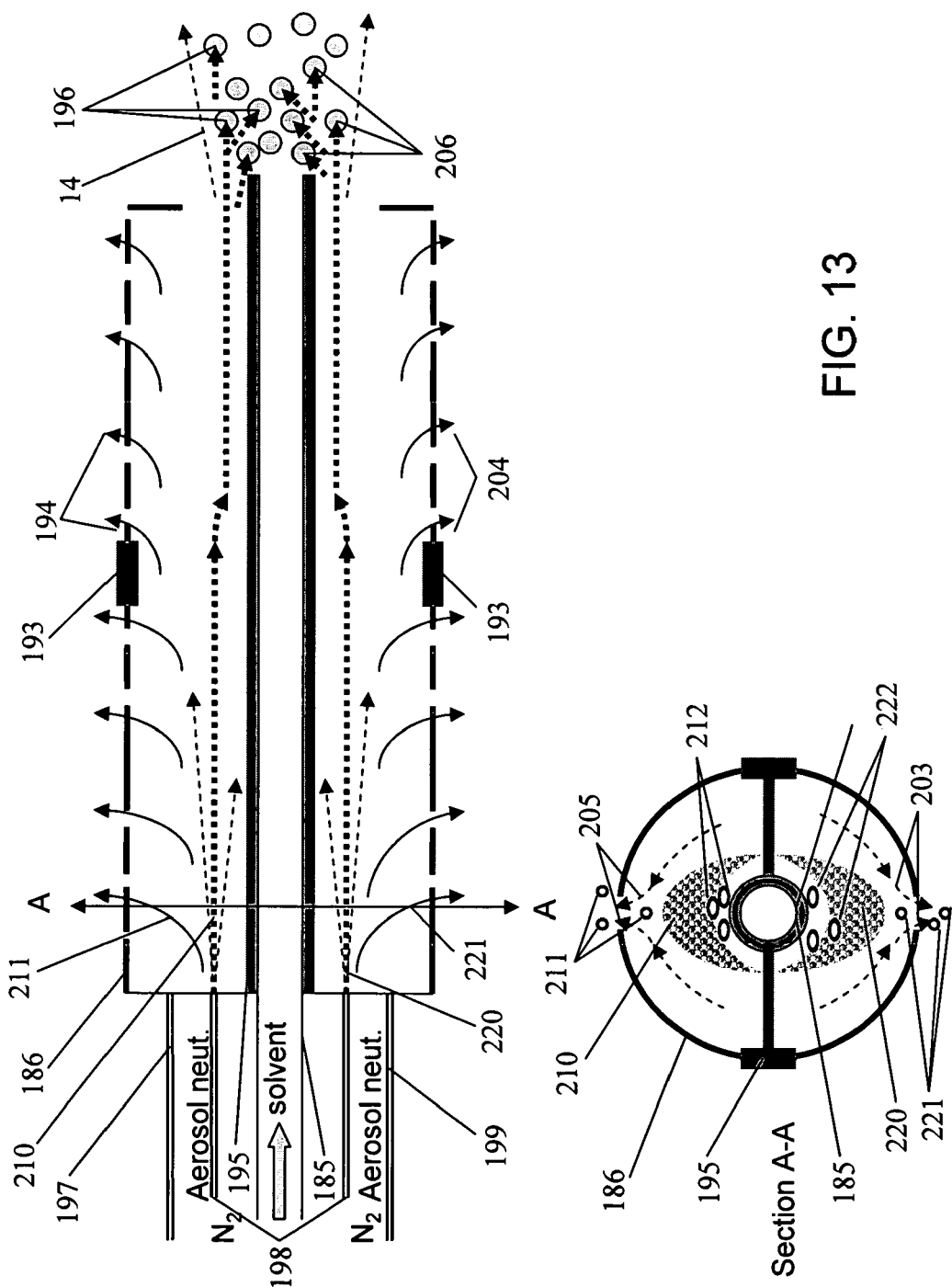
FIG. 13. Illustration of separation of charged aerosol particles before IM-TOFMS measurements.

Another important possibility is to use the basic principles of the electrospray ion source described above and to modify it for the investigation of aerosol particles. The aerosol particles nay be natural aerosols such as atmospheric aerosols or they may be generated aerosols. The proposed modification is illustrated in FIG. 11, FIG. 12 and FIG. 13. The left and the right parts of this source are the same as those previously described using the electrospray ion source see FIGS. 1B and 2. These parts have the same numerical identifiers as described for FIG. 2. The flow (40) with ions and neutrals is directed to the trapping region of the source shown in FIG. 1B.

Aerosol particles under the flow of ambient air by compressor (169) are directed inside the chamber (170) containing some layer of radioactive element (such as $^{210}$Po), e.g., as typically used in conventional instruments for aerosol analysis. Alpha particles of about 5 MeV energy produced by $^{210}$Po ionize air in chamber (170), create large amounts of positive and negative ions. These ions move in the chamber under influence of electric field orthogonal to initial flow of aerosol particles and charge these particles. Positively charged particles come to the right part of the chamber (170), negatively charged particles are concentrated at the left part of the chamber. The particles having zero total charge are moved by the gas flow to the bottom of the chamber (170) through the capillary (187) and are directed out of the chamber. By a computer controlled valve (189), they are moved away or mixed with nitrogen gas flow and enter separation chamber (186). Alternatively, they travel through capillaries (171) and (172) when computer controlled valve (189) is closed and valves (188) are open together with the flows. Positively and negatively charged particles travel to the top and bottom parts of the chamber (186) which is used both for separation of aerosol particles and for transporting of the nebulizer gas (being now a mixture of nitrogen with air and chosen part of aerosol particles) for producing droplets (12) of solvent from the capillary (185). Charged (positive are coming through the capillary (197), negative—through (199)) or neutral aerosol particles (together with nitrogen flow (198)) are moving with the nebulizer gas and are faster than solvent droplets so they can penetrate and accumulate inside droplets—(196) and (206); FIG. 13. Under the influence of solvent molecules and solvent ions, the organic substances adsorbed on the surface of the particle would become neutrals or ions in solution ready for further processing by the above-described electrospray technique. Sound frequency voltage applied to the solenoid (10), shown in more details in FIG. 1, provides energy into the droplets liquid flow around the aerosol particles and thus enhances removing of adsorbed substances from the surface of aerosol particles.

The cases of separation of charged aerosol particles and neutral ones are shown in FIG. 12 and FIG. 13. Separation of charged particles is provided by some version of FAIMS (Field Asymmetric Ion Mobility Spectrometry). Neutral particles are separated by gas flows due to differences in diffusion coefficients.

The cross-section of the chamber (186) for the case of charged particles separation is shown in bottom-left part of the FIG. 12. This chamber is divided into parts by insulator (195). The top part provides separation of positively charged aerosol particles, the bottom part separates negatively charged ones. An example of an asymmetric potential wave form (FAIMS) applied to the top part of the chamber (186) is shown (207) in FIG. 12. Reverse polarity wave-form (-FAIMS)—(208) is applied to the bottom part of the chamber (186). The position of the zero potential line may be changed to provide focusing of desired particles (190) and (200). Under the influence of an electric field provided by these wave forms and gas flows (205) and (203) only particles with some relation between their charge and size would be focused inside the chamber (186) in crescent-like shaped regions (190) and (200). Other particles would come out of the chamber (191) and (201) or concentrate around solvent capillary (185)—(192) and (202). To prevent loss of charge for these particles, a solvent capillary (185) is coated by an insulator (195). The potential of the solvent capillary (185) is usually maintained at around 0. To remove the particles (192) and (202) from the separation chamber (186) the potential wave forms applied to the right half of the chamber (186) are inverted in comparison to the left half. Insulator (193) separates these two parts. As a result the selected particles (190) and (200) come close to the solvent capillary and the particles concentrated there before (192) and (202) come out of the separation region (186)—(194) and (204). Thus charging of the droplets (196) and (206) by desired particles is provided and other particles are removed from the separation region (186).

Transport of neutral aerosol particles is shown in FIG. 13. These particles come into the separation chamber with the flow of nitrogen (210) and (220). Small particles with large diffusion coefficients (211) and (221) can quickly go out of the separation chamber (186). Larger particles with less diffusion coefficients would go further along the separation chamber and emerge from it (194) and (204) at some distance after their entrance point. The flow of relatively large particles (212) and (222) would come to the end of separation region to be caught by solvent droplets near the end of the capillary (185). By changing the pumping (174)—FIG. 12, it is possible to change the rate of separation of neutral aerosol particles and provide different size distribution of particles coming into the solvent droplets.

To simultaneously analyze the largest possible portion of the deflected charged or neutral aerosol particles it is possible to use two of the measuring units shown in FIG. 5. Their coupling to the described ion source is shown in FIG. 11. One possibility for producing ions from adsorbed organic substances is by using laser ablation from the beams (173). These beams are reflected from mirrors (168) to become parallel to the surface of the separation chamber (186) from where the considered particles (177) and (181) have appeared. Each output orifice for these particles is located opposite to some input funnel of the corresponding measuring unit. The volume between this surface and input funnels of the measuring units (the top one for analysis of positive ions and the bottom unit—for the negative ions) is pumped (174) to have in this region the pressure around 100 Torr. Electric fields (175) and (176) are applied to insert ions against gas flows (179) and (182) to ion traps (178) and (183) at the entrances of corresponding funnels. When the ion accumulation in traps is finished they are inserted inside mobility channels by pulse of strong electric field inside funnels to provide positive (180) and negative (184) mobility separating ion flows directed to corresponding multichannel orthogonal TOFMS.

It is possible to change the composition of the solution (1) to be mixed with the separated aerosol to contain additives which can enhance the ionization probability of the organics dissolved in the droplet after the droplet solvent extracts the aerosols. For example, the solution might contain MALDI matrix or could even be a suspension of nanoparticulates which may adsorb some of the organic analyte which had been on the surface of the aerosol.

Method of Combining Isotopic Labeling Followed by IM-TOFMS Analysis to Identify Unknown Molecular Complexes in Complex Systems.

The apparatus could be used for analysis of isotopically labeled drugs or other desired isotopically labeled analytes. For example, a precisely controlled mixture having a precisely determined composition comprising identical drug molecules (some precise portion of which are unlabeled (e.g., H) and the other portion of which are labeled on non-exchangeable sites with isotopes (e.g., D)), is introduced into a viable biological organism. Samples are later taken of the tissue, blood, serum, saliva, or whole cells, and analyzed. The ionized isotopic drug pairs appears in the plot of IM vs m/z as two ions separated in m/z by the precise difference between the mass of labeled and unlabelled drug but both types of ions have almost identical ion mobilities. This nearly identical mobility cross-section of isotopically labeled pairs of otherwise identical molecules can be use to search for drugs bound to unknown biomolecules (e.g. protein, lipid) by computer searching the plots of IM vs m/z from such samples. The drug/biomolecule complex will also be revealed by the nearly horizontal shift in m/z of the IM vs m/z plot due to the mass difference of the labeled and unlabelled drug. The recognition that the precise mass shift and the characteristic horizontal shift allows us to create a new approach to the identification of labeled molecules and their complexes with biomolecules. By creating an algorithm, we can search IM vs m/z plots for free drug in the midst of biological background, which might arise from direct analysis from complex biological samples such as tissue, saliva, blood, etc. Furthermore, the determination of metabolic products of the drug, and the binding of these metabolites or the binding of free drug with unknown biomolecules can also be identified by such a procedure. A further use of this method allows simultaneously relating the proteome, lipidome, and glycolipidome, to the metabolic products (metabolome) of a given sample. Yet a further use of the method is for measuring variations of the entire metabolome on a cell to cell basis from a biological cell culture by aerosolizing the cell from suspensions and measuring and correlating the IM-MS plots from each cell individually with one another. Such an approach, whether cell by cell or averaged over many cells, can be used when a cell culture is split and one half is grown with isotopically enriched nutrient such a specific peptide (e.g., deuterated leucine).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An apparatus for analyzing a sample, said apparatus comprising:
   a source for the generation of a flow of gaseous ions or a mixture of gaseous ions and gaseous neutral species from said sample, said source producing said flow in a first direction;
   an orthogonal collection region fluidly coupled to said source; and,
   at least one ion mobility assembly fluidly coupled to said source, said ion mobility assembly comprising a plurality of mobility tubes, wherein said ion mobility assembly has a separation axis which is orthogonal to said first direction.

2. The apparatus of claim 1, wherein said ion mobility assembly further comprises a plurality of CID tubes and a plurality of exit tubes, said CID tubes being fluidly coupled to said mobility tubes and said exit tubes being fluidly coupled to said CID tubes.

3. The apparatus of claim 2, wherein said ion mobility assembly further comprises at least one multichannel RF interface fluidly coupled to at least one of said CID tubes.

4. The apparatus of claim 3, wherein said at least one multichannel RF interface comprises pairs of rods and confining plates.

5. The apparatus of claim 1, wherein said ion mobility assembly further comprises at least one multichannel RF interface fluidly coupled to at least one of said mobility tubes.

6. The apparatus of claim 5, wherein said at least one multichannel RF interface comprises pairs of rods and confining plates.

7. The apparatus of claim 1, further comprising at least one TOFMS fluidly coupled to said ion mobility assembly.

8. The apparatus of claim 7, wherein said TOFMS comprises a position sensitive detector.

9. The apparatus of claim 7, wherein said at least one TOFMS is an oTOFMS.

10. The apparatus of claim 7, wherein said at least one TOFMS is a LoTOFMS.

11. The apparatus of claim 7, wherein said at least one TOFMS comprises a detector comprising a plurality of anodes in which two or more anodes of said plurality are each linked to single detector channels.

12. The apparatus of claim 11 wherein said single detector channel is a TDC channel.

13. The apparatus of claim 1, wherein said orthogonal collection region comprises one or more voltage grids.

14. The apparatus of claim 1, further comprising an ion trapping region fluidly coupled to said orthogonal collection region and to said ion mobility assembly, said ion trapping region comprising at least one ion trap.

15. The apparatus of claim 14, wherein one or more of said at least one ion trap is a DC field trap.

16. The apparatus of claim 14, wherein one or more of said at least one ion trap is an RF voltage trap.

17. The apparatus of claim 14, wherein said ion trapping region comprises a variable size exit orifice.

18. The apparatus of claim 14, further comprising a laser positioned to excite said gaseous ions or mixture of gaseous ions and gaseous neutral species in said ion trapping region, in said orthogonal collection region, or in both said ion trapping region and in said orthogonal collection region.

19. The apparatus of claim 14, further comprising means for a variable gas flow in said source, or in a region between said source and said ion mobility assembly, or in both.

20. The apparatus of claim 14, further comprising one or more mirrors in said region between said source and said ion mobility assembly.

21. The apparatus of claim 1, further comprising a laser positioned to excite said gaseous ions or mixture of gaseous ions and gaseous neutral species in said orthogonal collection region.

22. The apparatus of claim 21, wherein said orthogonal collection region comprises at least one voltage grid for each mobility tube.

23. The apparatus of claim 1, wherein said source is selected from the group consisting of a laser desorption source, a cluster bombardment source, a secondary ion source, a desorption electrospray ionization source an electrospray ionization source, photoionization source, and any combination thereof.

24. The apparatus of claim 23, wherein said source is a laser desorption source and said laser desorption source is a matrix assisted laser desorption ionization source.

25. The apparatus of claim 1, wherein said source comprises a droplet generator and is selected from the group consisting of electrospray source, a pneumo-spray source, an atmospheric pressure ionization source, a laserspray source, a vibrating orifice aerosol generator, and any combination thereof.

26. The apparatus of claim 1, further comprising means for a variable gas flow in one or more components of said ion mobility assembly.

27. The apparatus of claim 1, further comprising at least one funnel, said at least one funnel comprising electrode structures providing variable high and low electric fields, said at least one funnel positioned immediately before said at least one mobility tube.

28. The apparatus of claim 27, wherein said variable high and low electric fields comprise spatially alternating high and low electric fields.

29. The apparatus of claim 27, further comprising means for a variable gas flow in said at least one funnel.

30. The apparatus of claim 1, further comprising:
   at least one funnel, said at least one funnel comprising electrode structures providing variable high and low electric fields;
   at least one capillary electrode assembly; or,
   both said at least one funnel and said at least one capillary electrode assembly,
   wherein said at least one funnel and said at least on capillary electrode assembly are positioned at the exit of, or immediately after said at least one mobility tube.

31. The apparatus of claim 1, wherein one or more of said plurality of mobility tubes comprise electrode configurations producing periodic electric fields, hyperbolic electric fields or a combination of periodic and hyperbolic electric fields.

32. The apparatus of claim 1, wherein one or more of said plurality of mobility tubes comprises an entrance cone electrode.

33. The apparatus of claim 1, wherein said at least one ion mobility assembly comprises a plurality of ion mobility assemblies and wherein said plurality comprises at least one pair of ion mobility assemblies and wherein one ion mobility assembly of said pair is opposed to the other ion mobility assembly of said pair.

34. The apparatus of claim 1, wherein said source further comprises means to deliver a pH adjustor composition to said sample.

35. The apparatus of claim 34, wherein said apparatus further comprises a pH measuring device positioned in said source.

36. The apparatus of claim 1, wherein said source further comprises means to deliver a deuterated composition to said sample.

37. The apparatus of claim 1, further comprising a microwave voltage source coupled to said source.

38. The apparatus of claim 1, further comprising a sound frequency voltage source coupled to said source.

39. The apparatus of claim 1, wherein said source comprises an aerosol sampler, said aerosol sampler comprising a capillary and a chamber containing a radioactive element, said chamber operable to hold opposite charges near opposing walls of said chamber.

40. A method of analyzing a sample comprising the steps of:
creating a flow of gaseous ions or a mixture of gaseous ions and gaseous neutral species from said sample;
directing said flow into an orthogonal collection region;
orthogonally injecting said flow from said orthogonal collection region into at least one ion mobility assembly, said at least one ion mobility assembly comprising a plurality of mobility tubes;
and,
detecting said flow exiting said ion mobility assembly.

41. The method of claim 40, wherein said ion mobility assembly further comprises a plurality of CID tubes and a plurality of exit tubes.

42. The method of claim 40, wherein said ion mobility assembly further comprises at least one multi-channel RF interface.

43. The method of claim 40, wherein said ion mobility assembly further comprises at least one multi-channel RF interface.

44. The method of claim 40, wherein said step of detecting comprises detecting with at least one TOFMS, said TOFMS comprising a position sensitive detector.

45. The method of claim 44, wherein said step of detecting comprises detecting with at least one TOFMS comprises detecting with at least one oTOFMS.

46. The method of claim 44, wherein said step of detecting comprises detecting with at least one TOFMS comprises detecting with at least one LoTOFMS.

47. The method of claim 44, wherein said step of detecting comprises detecting with at least one TOFMS comprises detecting with at least one TOFMS comprising a detector comprising a plurality of anodes in which two or more anodes of said plurality are each linked to single detector channels.

48. The method of claim 47, wherein said single detector channel is a TDC channel.

49. The method of claim 40, wherein said step of directing said flow into an orthogonal collection region comprises directing said flow near or through one or more voltage grids.

50. The method of claim 40, wherein said step of directing said flow into an orthogonal collection region comprises directing said flow near or through one or more voltage grids.

51. The method of claim 50, wherein said step of directing comprises passing through at least one DC field trap.

52. The method of claim 50, wherein said step of directing comprises directing through at least one RF voltage trap.

53. The method of claim 50, wherein said step of directing comprises directing through a variable size exit orifice.

54. The method of claim 50, further comprising the step of irradiating said flow of gaseous ions or mixture of gaseous ions and gaseous neutral species with a laser, said step of irradiating being preformed in said ion trapping region, in said orthogonal collection region, or in both said ion trapping region and said orthogonal collection region.

55. The method of claim 50, further comprising the step of applying a variable gas flow to said flow of gaseous ions or mixture of gaseous ions and gaseous neutral species during said steps of creating, orthogonally injecting, or during both said steps of creating and orthogonally injecting.

56. The method of claim 50, further comprising the step of directing said flow of gaseous ions or mixture of gaseous ions and gaseous neutral species through one or more mirrors during said steps of creating, orthogonally injecting, or during both said steps of creating and orthogonally injecting.

57. The method of claim 40, wherein said step of creating comprises creating with a source selected from the group consisting of a laser desorption source, a cluster bombardment source, a secondary ion source, a desorption electrospray ionization source an electrospray ionization source, photoionization source, and any combination thereof.

58. The method of claim 57, wherein said step of creating with a laser desorption source comprises creating with a matrix assisted laser desorption ionization source.

59. The method of claim 40, wherein the said step of creating comprises creating droplets with a source selected from the group consisting of an electrospray source, a pneumo-spray source, an atmospheric pressure ionization source, a laserspray source, a vibrating orifice aerosol generator, and any combination thereof.

60. The method of claim 59, further comprising the step of splitting said droplets into positively and negatively charged droplets by quasi-resonant sound electric field or ultrasound frequency electric field.

61. The method of claim 59, further comprising the step of drying said droplets by ambient gas heating and microwave absorption.

62. The method of claim 40, further comprising the step of applying and varying a gas flow in one or more components of said ion mobility assembly.

63. The method of claim 40, further comprising the step of directing said flow through at least one funnel, said funnel positioned immediately before said at least one mobility tube, said at least one funnel comprising electrode structures providing variable and/or spatially alternating high and low electric fields.

64. The method of claim 63, further comprising:
varying a flow of gas in said at least one funnel;
varying polarity and/or magnitude of voltage across said funnels; or,
varying both said flow of gas and said polarity and/or magnitude of voltage.

65. The method of claim 40, further comprising the step of irradiating said flow of gaseous ions or mixture of gaseous ions and gaseous neutral species with laser radiation, said step of irradiating being preformed before said step of directing said flow into said orthogonal collection region.

66. The method of claim 65, further comprising the step of varying a flow of gas during said step of creating said flow of gaseous ions and neutral species.

67. The method of claim 65, wherein said step of irradiating comprises reflecting said laser radiation from one or more mirrors.

68. The method of claim 40, further comprising the step of applying periodic electric fields, hyperbolic electric fields of a combination of periodic and hyperbolic electric fields in one or more of said plurality of mobility tubes.

69. The method of claim 40, wherein one or more of said plurality of mobility tubes comprises an entrance cone electrode.

70. The method of claim 40, wherein said step of orthogonally injecting said flow into said at least one ion mobility assembly comprises orthogonally injecting said flow into a plurality of ion mobility assemblies and wherein said plurality comprises at least one pair of ion mobility assemblies wherein one ion mobility assembly of said pair is opposed to the other ion mobility assembly of said pair.

71. The method of claim 40, further comprising the step of delivering a pH adjustor composition to said sample.

72. The method of claim 71, wherein said step of delivering a pH adjustor comprises mixing said sample with flows of acid or base buffers or a combination of acid and base buffers.

73. The method of claim 71, wherein said step of delivering is regulated by a feedback signal.

74. The method of claim 73, wherein said feedback signal is generated by a pH measuring device.

75. The method of claim 71, wherein said step of detecting comprises detecting for samples at specific pH values.

76. The method of claim 40, further comprising the step of delivering a deuterated composition to said sample.

77. The method of claim 40, further comprising the step of applying a microwave voltage to said flow of gaseous ions or mixture of gaseous ions and gaseous neutral species.

78. The method of claim 40, further comprising the step of applying a sound frequency voltage to said flow of gaseous ions or mixture of gaseous ions and gaseous neutral species.

79. The method of claim 40, further comprising the step of collecting intensity data and correlating said intensity data from positive and negative ions to identify positive ion/negative ion pairs, wherein said intensity data is acquired from said step of detecting.

80. The method of claim 40, further comprising the step of collecting intensity data and correlating intensity data with the ion charge distribution of said sample, wherein said intensity data is acquired from said step of detecting.

81. The method of claim 40, wherein said step of creating further comprises generating an aerosol.

82. The method of claim 81, wherein said step of creating said flow of gaseous ions or mixture of gaseous ions and gaseous neutral species from said sample comprises creating said flow from an aerosol.

83. The method of claim 40, wherein said sample comprises a biological sample comprising non-exchangeable isotopically-labeled and non-isotopically-labeled chemical species and wherein said method further comprises using shifts in mass-to-charge ratio related to said isotopic labeling to analyze said biological sample.

84. The method of claim 83, wherein said chemical species is a drug.

85. The method of claim 83, wherein said chemical species is a known mixture of istotopically-labeled and unlabeled chemical species and said method further comprises correlating said shifts in mass-to-charge ratio to determine:

the mass of a chemical complex comprising said chemical species and one or more other unknown chemical species; and, the mass of said one or more other unknown chemical species.

* * * * *